United States Patent [19]
Bryans et al.

[11] Patent Number: 5,750,530
[45] Date of Patent: May 12, 1998

[54] PHARMACEUTICAL DIKETOPIPERAZINE COMPOUNDS

[75] Inventors: Justin Stephen Bryans; Adrian John Folkes; Christopher John Latham, all of Slough, United Kingdom

[73] Assignee: Xenova Limited, Berkshire, United Kingdom

[21] Appl. No.: 750,020

[22] PCT Filed: May 24, 1995

[86] PCT No.: PCT/GB95/01180

§ 371 Date: Dec. 17, 1996

§ 102(e) Date: Dec. 17, 1996

[87] PCT Pub. No.: WO95/32190

PCT Pub. Date: Nov. 30, 1995

[30] Foreign Application Priority Data

May 24, 1994 [GB] United Kingdom ............... 9410387

[51] Int. Cl.$^6$ .............. A61K 31/495; C07D 401/00; C07D 403/00
[52] U.S. Cl. ............. 514/255; 544/360; 544/363; 544/373; 544/379; 544/385
[58] Field of Search ............. 514/255; 544/360, 544/363, 373, 379, 385

[56] References Cited

FOREIGN PATENT DOCUMENTS

WO 94/04512  3/1994  WIPO .

OTHER PUBLICATIONS

T. Yokoi et al "Neihumici, a new cytotoxic . . ." Chemical Abstracts, vol. 109 No. 3, 1988, Columbus, Ohio. Abstract No. 16593a.

Primary Examiner—Matthew V. Grumbling
Assistant Examiner—Brenda Coleman
Attorney, Agent, or Firm—Nixon & Vanderhye

[57] ABSTRACT

A diketopiperazine of formula (I):

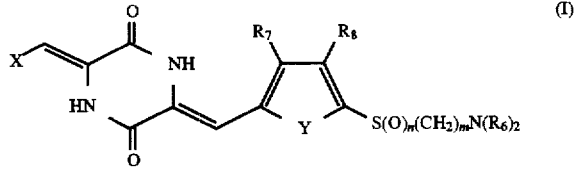

wherein each of $R_7$ and $R_8$ which may be the same or different; is hydrogen or a nitro group;

Y is

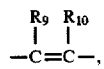

—O— or —S—, wherein each of $R_9$ and $R_{10}$ which may be the same or different, is hydrogen or a nitro group;

n is 0, 1 or 2;

m is an integer of 1 to 6;

each $R_6$, which may be the same or different, is a $C_1$–$C_6$ alkyl group; and X is selected from (i) a phenyl group of the following formula

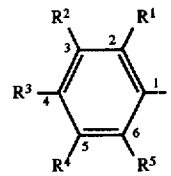

and the salts and esters thereof; have activity as inhibitors of plasminogen activator inhibitor.

9 Claims, No Drawings 5,750,530

PHARMACEUTICAL DIKETOPIPERAZINE COMPOUNDS

This application is a 371 of PCT/GB95/01180 filed May 24 1995.

The present invention relates to compounds useful as inhibitors of plasminogen activator inhibitor (PAI), to their preparation and to pharmaceutical and veterinary compositions containing them.

Plasminogen activators (PAs) are serine proteases which control the activation of the zymogen, plasminogen, to the active enzyme plasmin. Plasmin is important in a number of physiological and pathological processes including fibrinolysis, tissue remodelling, tumour growth and metastasis. The glycoprotein plasminogen activator inhibitor (PAI) is an endogenous fast-acting inhibitor of PA activity. PAI is a member of the serpin family and is synthesised by a variety of cells including endothelial cells. An imbalance between PAs and PAI contributes to a number of pathological conditions including haemostasis, inflammation, tumour growth and metastasis.

The present invention provides a diketopiperazine of formula (I):

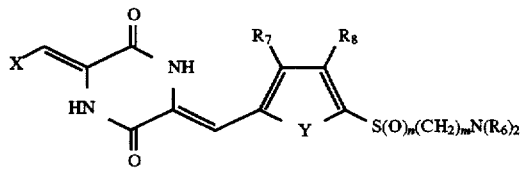

(I)

wherein each of $R_7$ and $R_8$ which may be the same or different, is hydrogen or a nitro group;

Y is

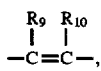

—O— or —S—, wherein each of $R_9$ and $R_{10}$, which may be the same or different, is hydrogen or a nitro group;

n is 0, 1 or 2;

m is an integer of 1 to 6;

each $R_6$, which may be the same or different, is a $C_1$–$C_6$ alkyl group; and X is selected from (i) a phenyl group of the following formula

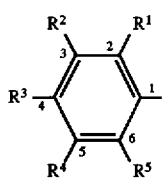

wherein each of $R_1$ to $R_5$, which may be the same or different, is independently selected from hydrogen, $C_1$–$C_6$ alkyl unsubstituted or substituted by one or more halogen atoms, $C_1$–$C_6$ alkoxy, $C_1$–$C_6$ alkythio, halogen, hydroxy, nitro, optionally substituted phenyl, nitrobenzyloxy, benzyloxy, cyano, —CH$_2$OH, —CH$_2$COOH, —CO$_2$R$^{11}$, —NHCOR$^{14}$, —NHSO$_2$R$^{13}$, —SO$_2$R$^{13}$, —CON(R$^{11}$R$^{12}$), —(CH$_2$)$_x$N(R$^{11}$R$^{12}$), —SOR$^{13}$, —SO$_2$N(R$^{11}$R$^{12}$), —N(R$^{11}$R$^{12}$), —O(CH$_2$)$_x$N(R$^{11}$R$^{12}$), —O(CH$_2$)$_x$CO$_2$R$^{11}$, —OCOR$^{11}$, —CH$_2$OCOR$^{11}$, —CH$_2$NHCOR$^{11}$, —CH$_2$NHCOOR$^{13}$, —CH$_2$SR$^{11}$, —CH$_2$SCOR$^{11}$, —CH$_2$S(O)$_y$R$^{13}$, —CH$_2$NHCO(CH$_2$)$_x$CO$_2$R$^{11}$, —N(R$^{11}$)COR$^{12}$, —NHCOCF$_3$, —NHCO(CH$_2$)$_x$CO$_2$R$^{11}$, —NHCO(CH$_2$)$_x$OCOR$^{11}$ and —NHCO(CH$_2$)$_x$OR$^{11}$ wherein x is 0 or is an integer of from 1 to 6, Y is 1 or 2, each of R$^{11}$ and R$^{12}$ is, independently, H or C$_1$–C$_6$ alkyl, R$^{13}$ is C$_1$–C$_6$ alkyl and R$^{14}$ is H, C$_1$–C$_6$ alkyl or a thiophene group; and/or any of R$_1$, and R$_2$, R$_2$ and R$_3$, R$_3$ and R$_4$ or R$_4$ and R$_5$ form, together with the carbon atoms to which they are attached, a furan group, a benzene ring which is optionally substituted or the cyclopentyl moiety of the group

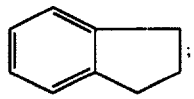

(ii) a heterocyclic ring selected from furan, thiophene, pyridine, quinoline and indole, the last of which is optionally N-substituted by C$_1$–C$_6$ alkyl;

(iii) a C$_1$–C$_6$ alkyl group, a 2,3-methylenedioxyphenyl group or a 3,4-methylenedioxyphenyl group; and (iv) a group —(CH$_2$)$_p$—Z wherein p is 0 or an integer of 1 to 4 and Z is a cyclohexyl group which optionally includes an unsaturated bond and/or a one or two carbon atom bridge, and is optionally substituted by one or more C$_1$–C$_6$ alkyl groups; or a pharmaceutically acceptable salt or ester thereof.

The numerals 1 to 6 denote ring positions on the phenyl group defined under (i) above.

A C$_1$–C$_6$ alkyl group is typically a C$_1$–C$_4$ alkyl group, for example a methyl, ethyl, propyl, i-propyl, n-butyl, sec-butyl or tert-butyl group. A halogen is, for example, fluorine, chlorine, bromine or iodine. A C$_1$–C$_6$ alkyl group substituted by halogen may be substituted by 1, 2 or 3 halogen atoms. It may be a perhaloalkyl group, for example trifluoromethyl.

A C$_1$–C$_6$ alkoxy group is typically a C$_1$–C$_4$ alkoxy group, for example a methoxy, ethoxy, propoxy, i-propoxy, n-butoxy, sec-butoxy or tert-butoxy group. A C$_1$–C$_6$ alkylthio group is typically a C$_1$–C$_4$ alkylthio group, for example methylthio, ethylthio, propylthio, i-propylthio, n-butylthio, sec-butylthio or tert-butylthio.

When the phenyl ring defined above under (i) is unsubstituted, each of R$_1$ to R$_5$ is hydrogen. When the ring is mono-substituted, di-substituted or tri-substituted then any one, two or three of the groups R$_1$ to R$_5$ is other than hydrogen. When the phenyl ring is mono-substituted, one of R$_1$ to R$_5$ is other than hydrogen, preferably R$_2$ or R$_3$, especially R$_3$. When the ring is mono-substituted one of R$_1$ to R$_5$ is preferably selected from a halogen, for instance fluorine; an alkoxy group, for instance OMe; and an acetamido group —NHAc in which Ac denotes acetyl.

The phenyl ring may also be 2,3-, 2,4-, 2,5-, 2,6-, 3,4- or 3,5- disubstituted or 2,3,4-, 2,3,5-, 2,3,6- or 3,4,5-trisubstituted. For example, three of R$_1$ to R$_5$ are hydrogen and two are other than hydrogen. For example R$_1$ and R$_2$, or R$_1$ and R$_3$, or R$_1$ and R$_4$, or R$_1$ and R$_5$, or R$_2$ and R$_3$, or R$_2$ and R$_4$ are other than hydrogen whilst, in each case, the other three of R$_1$ to R$_5$ are hydrogen.

Typically one of R$_7$ and R$_8$, and one of R$_9$ and R$_{10}$, is hydrogen or a nitro group.

When any two adjacent groups of R$_1$ to R$_5$ form, together with the carbon atoms to which they are attached, a benzene ring, that ring is either unsubstituted or substituted by any of the options specified above for R$_1$ to R$_5$. The resulting fused ring structure may be, for instance, a naphthalene or anthracene group. When any two adjacent groups of R$_1$ to R$_5$ form, together with the carbon atoms to which they are attached, a furan group, the resulting fused ring structure is a benzofuran group.

When X is as defined under (iv) above, p is typically 0 or 1 and Z is a cyclohexyl group. When the moiety Z includes a one or two carbon atom bridge it forms a bicycloheptyl or bicylooctyl ring, for example a bicyclo[3.1.1]heptyl or bicyclo[2.2.2]octyl ring. Z may also include at least one double bond and may be, for instance, a cyclohexenyl, bicyclo[3.1.1]heptenyl or bicyclo[2.2.2]octenyl group. When Z is substituted by one or more $C_1-C_6$, alkyl groups it may be mono- or di-substituted at any of positions 2 to 6 of the cyclohexyl ring or in the bridge or at the bridgehead.

In a preferred series of compounds of formula (I) in which X is a phenyl group, each of $R_1$ to $R_5$ is hydrogen.

In another preferred series of compounds, one of $R_1$ to $R_5$ is selected from alkoxy, $NHCOR^{11}$ and halogen and the other four of $R_1$ to $R_5$ are H. Alkoxy may be, for instance, OMe or $OBu^n$. $NHCOR^{11}$ is typically —NHAc. Halogen is typically F or Cl. Preferably $R_3$ is alkoxy, especially OMe or $OBu^n$; $NHCOR^{11}$, especially —NHAc; or halogen, especially F or Cl; and each of $R_1$, $R_2$, $R_4$ and $R_5$ is H.

In another series of preferred compounds in which X is a phenyl group, one or two of $R_1$ to $R_5$ are other than hydrogen whilst the others are hydrogen. For instance one of $R_1$, $R_2$ and $R_3$ is other than hydrogen. Alternatively $R_1$ and $R_3$, or $R_2$ and $R_3$, are other than hydrogen. Preferred values for the one or two of $R_1$ to $R_5$ which is or are other than hydrogen include alkoxy such as OMe or $OBu^n$, halogen such as Cl or F, hydroxy, $-N(R^{11}R^{12})$, $-CO_2R^{11}$, $-CH_2SCOR^{13}$, $-CH_2SR^{11}$, $-NHCOR^{11}$, $-O(CH_2)_nN(R^{11}R^{12})$, $-O(CH_2)_nCO_2R^{11}$, $-CH_2NHCO(CH_2)_nCO_2R^{11}$, $-NHCOCH_2OR^{11}$, $-NHCO(CH_2)_nOCOR^{11}$, $-CH_2NHCOOR^{13}$ and $CF_3$.

Particularly preferred compounds are those wherein $R_1$, $R_2$, $R_4$ and $R_5$ are each H and $R_3$ is selected from H, OMe and —NHAc. Alternatively each of $R_1$ to $R_5$ is independently selected from H, halogen, hydroxy, $C_1-C_6$ alkoxy, nitro, $-CH_2SCOR^{11}$, $-CH_2SR^{11}$, $-CO_2R^{11}$, $-OCOR^{13}$, $CF_3$, $-O(CH_2)_nN(R^{11}R^{12})$, $-O(CH_2)_nCO_2R^{11}$, $-CH_2NHCO(CH_2)_nCO_2R^{11}$, $-NHCO(CH_2)_nOR^{11}$, $-N(R^{11}R^{12})$, $-NHCO(CH_2)_nOCOR^{11}$, $-NHCO(CH_2)_n CO_2R^{11}$ and $-CH_2NHCO_2R^{13}$. Still more preferably, $R_1$ and $R_2$ are independently H, nitro or halogen, $R_3$ is H, hydroxy, $-O(CH_2)_nN(R^{11}R^{12})$, $-OCOR^{11}$, $-O(CH_2)_n CO_2R^{1}_{11}$, $-CH_2NHCO(CH_2)_nCO_2R^{11}$, $C_1-C_6$ alkoxy, $-NHCO(CH_2)_nOR^{11}$, $-NHCO(CH_2)_nOCOR^{11}$, $-N(R^{11}R^{12})$, $-CH_2NHCO_2R^{13}$, $-CH_2SR^{11}$ or $-NHCOR^{11}$; $R_4$ is H, halogen, $C_1-C_6$ alkoxy, $-CH_2SCOR^{11}$, $-CH_2SR^{11}$ or $-CO_2R^{11}$; and $R_5$ is H, nitro or halogen.

In one embodiment $R_3$ is NHAc, each of $R_1$, $R_2$, $R_4$ and $R_5$ is H. In a second embodiment $R_1$ is H or halogen such as Cl or F; $R_2$ is H, $R_3$ is halogen such as F or Cl, $C_1-C_6$ alkoxy such as OMe, $-N(R^{11}R^{12})$ such as $NMe_2$ or $-NHCOOR^{13}$ such as $-NHCOOBu^t$; $R_4$ is H and $R_5$ is halogen such as F, Cl, Br, or is $CF_3$.

In a third embodiment $R^1$ is H, nitro or halogen such as Cl; $R^2$ is H; $R_3$ is H, hydroxy, $-OCOR^{11}$ such as OAc, $-NHCO(CH_2)_nOCOR^{11}$ such as $-NHCOCH_2OAc$ or $-NHCOCH_2OR^{11}$ such as $-NHCOCH_2OH$; $R_4$ is H and $R_5$ is H or halogen such as F or Cl; or $R_2$ and $R_3$ form a benzene ring together with the carbon atoms to which they are attached.

In a fourth embodiment $R_1$ is H; $R_2$ is H and $R_3$ is $-CH_2SR^{11}$ such as $-CH_2SMe$, $-CH_2SCOR^{11}$ such as $-CH_2SAc$, $-NHCO(CH_2)_nCO_2R^{11}$ such as $-NHCO(CH_2)_3CO_2Me$, $-O(CH_2)_nCO_2R^{11}$ such as $-O(CH_2)_4CO_2H$, $-O(CH_2)N(R^{11}R^{12})$ such as $-O(CH_2)_3-NMe_2$, or $-N(R^{11}R^{12})$ such as $-NMe_2$ or $R_2$ is $-CH_2SCOR^{13}$ such as $-CH_2SAc$ or $-CH_2SR^{11}$ such as $-CH_2SH$ and $R_3$ is H; and $R_4$ and $R_5$ are both H.

When X is a heterocyclic ring it is preferably a 2-indole, 3-indole, 2-furan, 3-furan, 2-thiophene, 3-thiophene, 2-pyridine, 3-pyridine, 4-pyridine, 2-quinoline, 4-quinoline, 2-indole or 4-indole group. When the indole group is N-substituted by $C_1-C_6$ alkyl, it is preferably N-methyl substituted.

Preferred values for m are 2 and 3. At least one $R_6$ group is typically methyl. Preferably both groups $R_6$ are methyl.

One group of compounds of formula (I) have the following structure (A):

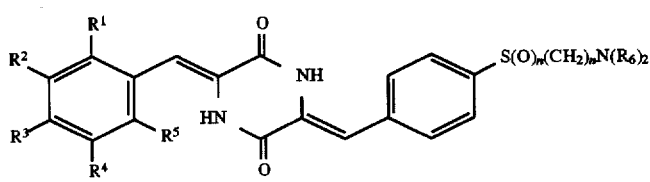

(A)

wherein $R_1$ to $R_6$ are as defined above, n is 0, 1 or 2 and m is 2 or 3. Typically each of $R_1$ to $R_5$ is hydrogen.

Another group of compounds of formula (I) have the following structure (B):

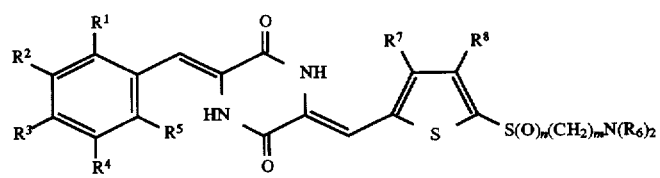

(B)

wherein $R_1$ to $R_8$ are as defined above, n is 0, 1 or 2 and m is 2 or 3. Typically each of $R_1$ to $R_5$ is hydrogen.

A third group of compounds of formula (I) have the following structure (C):

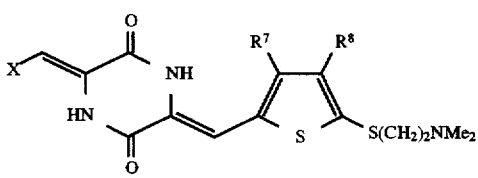

(C)

wherein X, R₇ and R₈ are as defined above for formula (I).

Examples of specific compounds of formula (I) are as follows. The compound numbering given in brackets is adhered to in the rest of the specification. Unless specifically allocated a separate number, the hydrochloride salts of compounds of formula (I) are referred to herein using the suffix ".HCl" following the number of the corresponding free base.

(3Z,6Z)-3-(3-Chlorobenzylidene)-6-(4-(2-dimethylaminoethylthio)benzylidene)-2,5-piperazinedione (5292)

(3Z,6Z)-3-(4-Dimethylaminobenzylidene)-6-(4-(2-dimethylaminoethylthio)benzylidene)-2,5-piperazinedione (5424)

(3Z,6Z)-3-(3-Bromobenzylidene)-6-(4-(2-dimethylaminoethylthio)benzylidene)-2,5-piperazinedione (5425)

(3Z,6Z)-3-(4-Chlorobenzylidene)-6-(4-(2-dimethylaminoethylthio)benzylidene)-2,5-piperazinedione (5437)

(3Z,6Z)-3-(4-Cyanobenzylidene)-6-(4-(2-dimethylaminoethylthio)benzylidene)-2,5-piperazinedione (5462)

(3Z,6Z)-3-(3,4-Dichlorobenzylidene)-6-(4-(2-dimethylaminoethylthio)benzylidene)-2,5-piperazinedione (5465)

(3Z,6Z)-3-(3-Cyanobenzylidene)-6-(4-(2-dimethylaminoethylthio)benzylidene)-2,5-piperazinedione (5476)

(3Z,6Z)-3-(4-Bromobenzylidene)-6-(4-(2-dimethylaminoethylthio)benzylidene)-2,5-piperazinedione (5480)

(3Z,6Z)-3-(4-Benzyloxybenzylidene)-6-(4-(2-dimethylaminoethylthio)benzylidene)-2,5-piperazinedione (5481)

(3Z,6Z)-3-(3-Benzyloxybenzylidene)-6-(4-(2-dimethylaminoethylthio)benzylidene)-2,5-piperazinedione (5486)

(3Z,6Z)-3-(4-(2-Dimethylaminoethylthio)benzylidene)-6-(4-trifluoromethylbenzylidene)-2,5-piperazinedione (5294)

(3Z,6Z)-3-(4-(2-Dimethylaminoethylthio)benzylidene)-6-(4-nitrobenzylidene)-2,5-piperazinedione (5461)

(3Z,6Z)-3-(4-(2-Dimethylaminoethylthio)benzylidene)-6-(4-methylthiobenzyidene)-2,5-piperazinedione (5426)

(3Z,6Z)-3-(4-(2-Dimethylaminoethylthio)benzylidene)-6-(4-tert-butylbenzylidene)-2,5-piperazinedione (5440)

(3Z,6Z)-3-(4-(2-Dimethylaminoethylthio)benzylidene)-6-(4-methylbenzylidene)-2,5-piperazinedione (5463)

(3Z,6Z)-3-(4-(2-Dimethylaminoethylthio)benzylidene)-6-(4-methoxycarbonylbenzylidene)-2,5-piperazinedione (5478)

(3Z,6Z)-3-(4-(2-Dimethylaminoethylthio)benzylidene)-6-(4-methoxybenzylidene)-2,5-piperazinedione (5479)

(3Z,6Z)-6-(4-(2-Dimethylaminoethylthio)benzylidene)-3-(3-furylmethylene)-2,5-piperazinedione (5129)

(3Z,6Z)-6-(4-(2-Dimethylaminoethylthio)benzylidene)-3-(3-thienylmethylene)-2,5-piperazinedione (5133)

(3Z,6Z)-6-(4-(2-Dimethylaminoethylthio)benzylidene)-3-(2-naphthylmethylene)-2,5-piperazinedione (5284)

(3Z,6Z)-6-(4-(2-Dimethylaminoethylthio)benzylidene)-3-(3-nitrobenzylidene)-2,5-piperazinedione (5422)

(3Z,6Z)-6-(4-(2-Dimethylaminoethylthio)benzylidene)-3-(3-trifluoromethylbenzylidene)-2,5-piperazinedione (5423)

(3Z,6Z)-6-(4-(2-Dimethylaminoethylthio)benzylidene)-3-(3-methoxybenzylidene)-2,5-piperazinedione (5438)

(3Z,6Z)-6-(4-(2-Dimethylaminoethylthio)benzylidene)-3-(3-methylbenzylidene)-2,5-piperazinedione (5439)

(3Z,6Z)-6-(4-(2-Dimethylaminoethylthio)benzylidene)-3-(3-methoxy-4-(4-nitrobenzyloxy)benzylidene)-2,5-piperazinedione (5490)

(3Z,6Z)-6-(4-(2-Dimethylaminoethylthio)benzylidene)-3-(3,4-methylenedioxybenzylidene)-2,5-piperazinedione (5491)

(3Z,6Z)-6-(4-(2-Dimethylaminoethylthio)benzylidene)-3-(1-methyl-3-indolyl)methylene-2,5-piperazinedione (5497)

(3Z,6Z)-6-Benzylidene-3-(4-(2-dimethylaminoethylthio)benzylidene)-2,5-piperazinedione (5128)

(3Z,6Z)-6-Benzylidene-3-(4-(2-dimethylaminoethylsulphinyl)benzylidene)-2,5-piperazinedione (5141)

(3Z,6Z)-6-Benzylidene-3-(4-(2-dimethylaminoethylthio)-3-nitrobenzylidene)-2,5-piperazinedione (5400)

(3Z,6Z)-3-(5-(2-Dimethylaminoethylthio)-2-thienyl)methylene-6-(3-thienyl)methylene-2,5-piperazinedione (5257)

(3Z,6Z)-3-(5-(2-Dimethylaminoethylthio)-2-thienyl)methylene-6-(3,4-methylenedioxybenzylidene)-2,5-piperazinedione (5279)

(3Z,6Z)-3-(5-(2-Dimethylaminoethylthio)-2-thienyl)methylene-6-(2-naphthyl)methylene-2,5-piperazinedione (5286)

(3Z,6Z)-3-(5-(2-Dimethylaminoethylthio)-2-thienyl)methylene-6-(4-trifluoromethylbenzylidene)-2,5-piperazinedione (5293)

(3Z,6Z)-3-(5-(2-Dimethylaminoethylthio)-2-thienyl)methylene-6-(2-fluorenylmethylene)-2,5-piperazinedione (5301)

(3Z,6Z)-6-(5-(2-Dimethylaminoethylthio)-2-thienyl)methylene-3-(4-quinolylmethylene)-2,5-piperazinedione (5307)

(3Z,6Z)-6-(5-(2-Dimethylaminoethylthio)-2-thienyl)methylene-3-(2-quinolylmethylene)-2,5-piperazinedione (5308)

(3Z,6Z)-3-(5-(2-Dimethylaminoethylthio)-2-thienyl)methylene-6-(3-methoxybenzylidene)-2,5-piperazinedione (5314)

(3Z,6Z)-3-(5-(2-Dimethylaminoethylthio)-2-thienyl)methylene-6-(3-trifluoromethylbenzylidene)-2,5-piperazinedione (5315)

(3Z,6Z)-3-(5-(2-Dimethylaminoethylthio)-2-thienyl)methylene-6-(3-nitrobenzylidene)-2,5-piperazinedione (5316)

(3Z,6Z)-3-(5-(2-Dimethylaminoethylthio)-2-thienyl)methylene-6-(4-nitrobenzylidene)-2,5-piperazinedione (5428)

(3Z,6Z)-3-(5-(2-Dimethylaminoethylthio)-2-thienyl)methylene-6-(4-methylthiobenzylidene)-2,5-piperazinedione (5429)

(3Z,6Z)-3-(5-(2-Dimethylaminoethylthio)-2-thienyl)methylene-6-(4-tert-butylbenzylidene)-2,5-piperazinedione (5430)

(3Z,6Z)-3-(5-(2-Dimethylaminoethylthio)-2-thienyl)methylene-6-(2-methylpropylidene)-2,5-piperazinedione (5448)

(3Z,6Z)-3-(5-(2-Dimethylaminoethylthio)-2-thienyl)methylene-6-(2-(3,3-dimethylcyclohexyl)ethylidene)-2,5-piperazinedione (5455)

(3Z,6Z)-3-(5-(2-Dimethylaminoethylthio)-2-thienyl) methylene-6-(4-methylbenzylidene)-2,5-piperazinedione (5460)

(3Z,6Z)-3-(5-(2-Dimethylaminoethylthio)-2-thienyl) methylene-6-(4-methoxybenzylidene)-2,5-piperazinedione (5464)

(3Z,6Z)-3-(5-(2-Dimethylaminoethylthio)-2-thienyl) methylene-6-(4-methoxycarbonylbenzylidene)-2,5-piperazinedione (5477)

(3Z,6Z)-3-(5-(2-Dimethylaminoethylthio)-2-thienyl) methylene-6-(3-methoxy-4-(4-nitrobenzyloxy) benzylidene)-2,5-piperazinedione (5488)

(3Z,6Z)-3-(5-(2-Dimethylaminoethylthio)-2-thienyl) methylene-6-(2-methoxy-1-naphthyl)methylene-2,5-piperazinedione (5499)

(3Z,6Z)-3-(5-(2-Dimethylaminoethylthio)-2-thienyl) methylene-6-(3,3-dimethyl-1-butylidene)-2,5-piperazinedione (5502)

(3Z,6Z)-3-(5-(2-Dimethylaminoethylthio)-2-thienyl) methylene-6-(4-(2-thiophenecarboxamido)benzylidene)-2,5-piperazinedione (5507)

(3Z,6Z)-6-(5-(2-Dimethylaminoethylthio)-2-thienyl) methylene-3-(3-pyridylmethylene)-2,5-piperazinedione (5470)

(3Z,6Z)-6-(5-(2-Dimethylaminoethylthio)-2-thienyl) methylene-3-(2-pyridylmethylene)-2,5-piperazinedione (5471)

(3Z,6Z)-6-(5-(2-Dimethylaminoethylthio)-2-thienyl) methylene-3-(4-pyridylmethylene)-2,5-piperazinedione (5472)

(3Z,6Z)-6-(5-(2-Dimethylaminoethylthio)-2-thienyl) methylene-3-(1-methyl-3-indolyl)methylene-2,5-piperazinedione (5473)

(3Z,6Z)-6-Benzylidene-3-(5-(2-diisopropylaminoethylthio)-2-thienyl)methylene-2,5-piperazinedione (5399)

(3Z,6Z)-6-Benzylidene-3-(5-(2-dimethylaminoethylthio)-4-nitro-2-thienyl)methylene-2,5-piperazinedione (5403)

(3Z,6Z)-3-(2,3-dihydro-5-benzofuranyl)methylene-6-(5-(2-dimethylaminoethylthio)-2-thienyl)methylene-2,5-piperazinedione (5311)

(3Z,6Z)-6-Benzylidene-3-(5-(2-dimethylaminoethylthio)-2-thienyl)methylene-2,5-piperazinedione (5131)

(3Z,6Z)-6-(4-Dimethylaminobenzylidene)-3-(5-(2-dimethylaminoethylthio)-2-thienyl)methylene-2,5-piperazinedione (5280)

(3Z,6Z)-6-(4-Acetamidobenzylidene)-3-(5-(2-dimethylaminoethylthio)-2-thienyl)methylene-2,5-piperazinedione (5300)

(3Z,6Z)-6-(3-Chlorobenzylidene)-3-(5-(2-dimethylaminoethylthio)-2-thienyl)methylene-2,5-piperazinedione (5291)

(3Z,6Z)-6-(2-Bromobenzylidene)-3-(5-(2-dimethylaminoethylthio)-2-thienyl)methylene-2,5-piperazinedione (5313)

(3Z,6Z)-6-(4-Chlorobenzylidene)-3-(5-(2-dimethylaminoethylthio)-2-thienyl)methylene-2,5-piperazinedione (5427)

(3Z,6Z)-6-(4-Cyanobenzylidene)-3-(5-(2-dimethylaminoethylthio)-2-thienyl)methylene-2,5-piperazinedione (5431)

(3Z,6Z)-6-(3,4-Dichlorobenzylidene)-3-(5-(2-dimethylaminoethylthio)-2-thienyl)methylene-2,5-piperazinedione (5432)

(3Z,6Z)-6-(3-Bromobenzylidene)-3-(5-(2-dimethylaminoethylthio)-2-thienyl)methylene-2,5-piperazinedione (5433)

(3Z,6Z)-6-(3-Cyanobenzylidene)-3-(5-(2-dimethylaminoethylthio)-2-thienyl)methylene-2,5-piperazinedione (5434)

(3Z,6Z)-6-Cyclohexylmethylene-3-(5-(2-dimethylaminoethylthio)-2-thienyl)methylene-2,5-piperazinedione (5454)

(3Z,6Z)-6-(4-Benzyloxybenzylidene)-3-(5-(2-dimethylaminoethylthio)-2-thienyl)methylene-2,5-piperazinedione (5482)

(3Z,6Z)-6-(3-Benzyloxybenzylidene)-3-(5-(2-dimethylaminoethylthio)-2-thienyl)methylene-2,5-piperazinedione (5487)

(3Z,6Z)-6-(4-Bromobenzylidene)-3-(5-(2-dimethylaminoethylthio)-2-thienyl)methylene-2,5-piperazinedione (5489)

(3Z,6Z)-6-(9-Anthrylmethylene)-3-(5-(2-dimethylaminoethylthio)-2-thienyl)methylene-2,5-piperazinedione (5498)

(3Z,6Z)-6-Benzylidene-3-(5-(6-dimethylaminohexylthio)-2-thienyl)methylene-2,5-piperazinedione (5442)

(3Z,6Z)-6-Benzylidene-3-(5-(2-dimethylaminoethylthio)-2-furyl)methylene-2,5-piperazinedione (5253)

(3Z,6Z)-3-(5-(2-Dimethylaminoethylthio)-2-thienyl) methylene-6-(6,6-dimethyl-bicyclo[3.1.1]hept-2-enyl) methylene-2,5-piperazinedione (5508)

Compounds of formula (I) may be prepared by a process which comprises either (i) condensing a compound of formula (II)

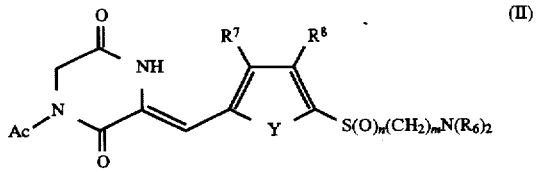

wherein Y, $R_6$, $R_7$, $R_8$, n and m are as defined above, with a compound of formula (III):

wherein X is as defined above and wherein any of the substituents on X is optionally protected, in the presence of a base in an organic solvent; or (ii) condensing a compound of formula (IV):

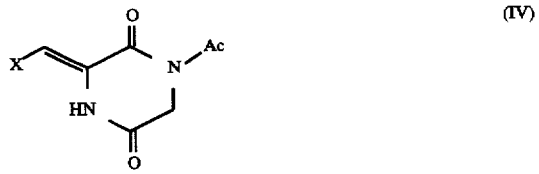

wherein X is as defined above and wherein any of the substituents on X is optionally protected, with a compound of formula (V):

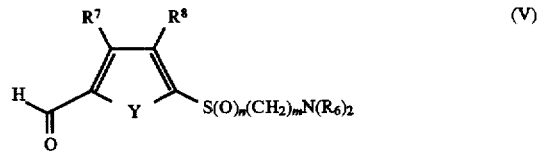

wherein Y, $R_6$, $R_7$, $R_8$, n and m are as defined above, in the presence of a base in an organic solvent; and, in either case (i) or (ii), if required, removing optionally present protecting groups and/or, if desired, converting one compound of formula (I) into another compound of formula (I), and/or, if desired, converting a compound of formula (I) into a pharmaceutically acceptable salt or ester thereof, and/or, if desired, converting a salt or ester into a free compound, and/or, if desired, separating a mixture of isomers of compounds of formula (I) into the single isomers.

A compound of formula (I) produced directly by the condensation reaction between (II) and (III) or (IV) and (V) may be modified, if desired, by converting one or more of the substituent groups on X into different substituent groups. These optional conversions may be carried out by methods known in themselves. For example, a compound of formula (III) or (IV) in which X bears one or more substituents which is an ester group may be converted to a compound of formula (I) wherein the corresponding substituent is a free —COOH group, by acid or alkaline hydrolysis at a suitable temperature, for example from ambient temperature to 100° C.

A compound of formula (I) in which one or more of the substituent groups on X is a —$CO_2H$ group may be converted into a compound of formula (I) wherein the corresponding substituent is esterified by esterification, for example by treating the carboxylic acid with a suitable $C_1$–$C_6$ alkyl alcohol in the presence of 1,3-dicyclohexylcarbodiimide in an inert solvent.

A compound of formula (I) in which one or more of the substituent groups on X is a free —$CO_2H$ group may be converted into a compound of formula (I) in which the corresponding substituent is a group —$CON(R^{11}R^{12})$, wherein $R^{11}$ and $R^{12}$ are as defined above, for example by treatment with ammonia or an amine in the presence of 1,3-dicyclohexylcarbodiimide in an inert solvent.

A compound of formula (I) in which one or more of the substituent groups on X is a free —$CO_2H$ group may be converted into a compound of formula (I) wherein the corresponding substituent is a —$CH_2OH$ group by reduction, for example using borane in a suitable solvent such as tetrahydrofuran.

Protecting groups for any of the substituents on group X in compounds of formulae (III) or (IV) are optionally introduced prior to step (i) or step (ii) when any of groups $R_1$ to $R_5$ are groups which are sensitive to the condensation reaction conditions or incompatible with the condensation reaction, for example a —COOH, —$CH_2OH$ or amino group. The protecting groups are then removed at the end of the process. Any conventional protecting group suitable for the group in question may be employed, and may be introduced and subsequently removed by well-known standard methods.

The condensation reaction between compounds (II) and (III) or (IV) and (V) is suitably performed in the presence of a base which is potassium t-butoxide, sodium hydride, potassium carbonate, sodium carbonate, caesium carbonate, sodium acetate, potassium fluoride on alumina, or triethylamine in a solvent such as dimethylformamide, or in the presence of potassium t-butoxide in t-butanol or a mixture of t-butanol and dimethylformamide. The reaction is typically performed at a temperature between 0° C. and the reflux temperature of the solvent. Typically the base is caesium carbonate, the solvent is dimethylformamide and the temperature is about 90° C.

The compounds of formula (II) may be prepared by a process comprising reacting 1,4-diacetyl-2,5-piperazinedione with a compound of formula (V) as defined above, in the presence of a base in an organic solvent. Similarly, the compounds of formula (IV) may be prepared by a process which comprises reacting 1,4-diacetyl-2,5-piperazinedione with a compound of formula (III) as defined above, in the presence of a base in an organic solvent. Typically the base is postassium t-butoxide/butanol, the solvent is THF and the reaction temperature is from 0° C. to room temperature.

If necessary, the resulting compound of formula (II) or (IV) can be separated from other reaction products by chromatography.

The reaction of 1,4-diacetyl-2,5-piperazinedione with the compound of formula (V) or (III) is suitably performed under the same conditions as described above for the condensation between compounds (II) and (III), or (IV) and (V).

The substituted benzaldehydes of formulae (III) and (V) are known compounds, or can be prepared from readily available starting materials by conventional methods, for example by analogy with the methods described in Reference Examples 2, 3 and 6 to 10 which follow. For instance, a compound of formula (V) may be prepared by treating a compound of formula (VI):

$$HS(O)_n(CH_2)_mN(R_6)_2 \quad (VI)$$

wherein n is 0 and m and $R_6$ are as defined above, or an acid addition salt thereof, with a compound of formula (VII):

(VII)

wherein Y is as defined above and Z is a leaving group, in the presence of a base in an organic solvent. Z is, for example, a halogen such as bromine or a nitro group. The base may be, for instance, sodium hydride and the organic solvent may be dimethyl sulphoxide (DMSO).

Compounds of formula (I), (II) or (V) wherein n is 1 or 2 may be prepared from the corresponding compound of formula (I), (II) or (V) wherein n is 0 by oxidation. Any conventional oxidation conditions may be employed. A suitable oxidising agent is, for example, sodium periodate. Reference Example 5 illustrates such a process.

The 1,4-diacetyl-2,5-piperazinedione used as a starting material in the preparation of compounds of formulae (II) and (IV) may be prepared by treating 2,5-piperazinedione (glycine anhydride) with an acetylating agent. The acetylation may be performed using any conventional acetylating agent, for example acetic anhydride under reflux or, alternatively, acetic anhydride at a temperature below reflux in the presence of 4-dimethylaminopyridine.

Compounds of formula (I) may also be prepared by a process comprising the microwave irradiation of (i) a mixture comprising a compound of formula (II) as defined above, a compound of formula (III) and potassium fluoride on alumina, or (ii) a mixture comprising a compound of formula (IV) a compound of formula (V) and potassium fluoride on alumina, or (iii) a mixture comprising 1,4-diacetyl-2,5-piperazinedione, a compound of formula (III), a compound of formula (V) and potassium fluoride on alumina. The irradiation is performed in the absence of a solvent.

Compounds of formula (I) may also be obtained directly by a process which comprises condensing together 1,4-diacetyl-2,5-piperazinedione, a compound of formula (III) and a compound of formula (V) in the presence of a base in an organic solvent. Suitable bases, solvents and reaction conditions are as described above for the condensation reaction between, for example, compounds (II) and (III).

An alternative direct process for the preparation of compounds of formula (I) comprises condensing together 2,5-piperazinedione, a compound of formula (III) and a compound of formula (V) in the presence of sodium acetate and acetic anhydride at elevated temperature, for example under reflux.

An alternative process for the preparation of compounds of formula (II) comprises treating a compound of formula (VIII):

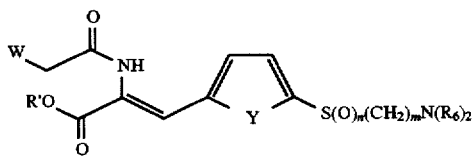

wherein n, m and $R_6$ are as defined above, W is a halogen and R' is a $C_1$–$C_6$ alkyl group, with ammonia followed by acetic anhydride.

Compounds of formula (IV) may be prepared by an analogous process which comprises treating a compound of formula (IX):

wherein X, W and R' are as defined above, with ammonia followed by acetic anhydride.

W in formula (VIII) or (IX) is typically iodine. R' is, for example, a $C_1$–$C_4$ alkyl group such as a methyl, ethyl, propyl, i-propyl, butyl, sec-butyl or tert-butyl group.

A review of synthetic approaches to unsaturated 3-monosubstituted and 3,6-disubstituted-2,5-piperazinediones is provided in Heterocycles, 1983, 20, 1407 (C. Shin).

Compounds of formula (I) may be optionally washed after any of the above preparative procedures with one or more of the following: water, ethanol, ethyl acetate and diethyl ether.

Where appropriate compounds of formula (I) may be optionally recrystallised from a suitable solvent such as methanol.

Compounds of formula (I) may be converted into pharmaceutically acceptable salts, and salts may be converted into the free compound, by conventional methods. Suitable salts include salts with pharmaceutically acceptable, inorganic or organic acids.

Examples of inorganic acids include hydrochloric acid, sulphuric acid and orthophosphoric acid. Examples of organic acids include p-toluenesulphonic acid, methanesulphonic acid, mucic acid and succinic acid.

Hydrochloride salts, for example, may be prepared by bubbling gaseous HCl through a solution of the compound in dry THF or DMF.

The diketopiperazines of formula (I) and their pharmaceutically acceptable salts and esters (referred to hereinafter as the "present compounds") have utility as inhibitors of PAI. Elevated levels of PAI-1, by reducing the net endogenous fibrinolytic capacity, can contribute to the pathogenesis of various thrombotic disorders including myocardial infarction, deep vein thrombosis and disseminated intravascular coagulation. The present compounds therefore can act as inhibitors of the tPA/PAI-1 interaction. The present compounds can be used in the treatment of haemostatic disorders. A human or animal, e.g. a mammal, can therefore be treated by a method comprising administration of a therapeutically effective amount of a diketopiperazine of formula (I) or a pharmaceutically or veterinarily acceptable salt thereof.

Tissue plasminogen activator (tPA) is used as a fibrinolytic agent in the treatment of thrombotic disorders. The efficacy of the tPA in this role may be enhanced if it is administered together with a PAI inhibitor. A human or animal, e.g. a mammal, can therefore be treated by a method comprising the combined administration of a therapeutically effective amount of tPA and a therapeutically effective amount of any one of the present compounds. The present invention also provides products containing a diketopiperazine of formula (I) or a pharmaceutically acceptable salt or ester thereof and tPA as a combined preparation for simultaneous, separate or sequential use in the treatment of thrombotic disorders, for example where there is inappropriate PAI activity. In such products the present compound is formulated for oral or parenteral (intravenous, intramuscular or subcutaneous) administration and the tPA is formulated for intravenous administration.

As one example, during acute myocardial infarction (MI) one of the present compounds may be administered to a patient together with tPA to enhance the efficacy of the tPA treatment. As a further example, early re-occlusion following treatment of a patient with tPA may be prevented by the post-MI administration of one of the present compounds.

The present compounds have been tested in a PAI functional assay. In this assay, a compound is incubated with PAI-1 prior to addition to the tPA assay system. Inhibition of PAI-1 results in the production of plasmin from plasminogen. In turn, plasmin cleaves the chromogenic substrate S2251 (Kabi Vitrum) producing pNA (p-nitroaniline) which is detected spectrophotometrically at 405 nm (K. Nilsson et al, Fibrinolysis (1987) 1, 163–168). The results of the assay are reported below.

The present compounds can be administered in a variety of dosage forms, for example orally such as in the form of tablets, capsules, sugar- or film-coated tablets, liquid solutions or suspensions or parenterally, for example intramuscularly, intravenously or subcutaneously. The present compounds may therefore be given by injection or infusion.

The dosage depends on a variety of factors including the age, weight and condition of the patient and the route of administration. Typically, however, the dosage adopted for each route of administration when a compound of the invention is administered alone to adult humans is 0.001 to 10 mg/kg, most commonly in the range of 0.01 to 5 mg/kg, body weight. Such a dosage may be given, for example, from 1 to 5 times daily by bolus infusion, infusion over several hours and/or repeated administration.

When one of the present compounds is administered in combination with tPA to adult humans, the dosage adopted for each route of administration is typically from 0.001 to 10 mg, more typically 0.01 to 5 mg per kg body weight for a compound of the invention and from 5 to 500 mg administered intravenously for the tPA. A suitable dosage regimen for the tPA is 100 mg given intravenously over 3 hours as follows: 10% of the total dose as an i.v. bolus over 1–2 minutes, 50% of the total dose as an infusion over 1 hour, 40% of the total dose as an infusion over the subsequent 2 hours.

A diketopiperazine of formula (I) or a pharmaceutically acceptable salt or ester thereof is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. An agent for use as an inhibitor of PAI comprising any one of the present compounds is therefore provided.

For example, the solid oral forms may contain, together with the active compound, diluents such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures; dyestuffs, sweeteners; wetting agents such as lecithin, polysorbates, lauryl sulphates. Such preparations may be manufactured in known manners, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular, a syrup for diabetic patients can contain as carriers only products, for example sorbitol, which do not metabolise to glucose or which only metabolise a very small amount to glucose. The suspensions and the emulsions may contain as carrier, for example, a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, and, if desired, a suitable amount of lidocaine hydrochloride. Some of the present compounds are insoluble in water. Such compounds may be encapsulated within liposomes.

The following Examples illustrate the invention:

REFERENCE EXAMPLE 1

Preparation of 1-acetyl-3-benzylidene-2,5-piperazinedione 1,4-Diacetyl-2,5-piperazinedione (25.0 g, 126 mmol) was heated at 120°–130° C. in DMF (200 ml) with triethylamine (17.6 ml, 126 mmol) and benzaldehyde (13.0 ml, 126 mmol). After 4 h the mixture was cooled to room temperature and poured into EtOAc (1000 ml), and washed three times with brine. Any solid formed at this stage was filtered off. The filtrate was dried (MgSO$_4$) and the solvent removed in vacuo. The residue was recrystallised from EtOAc:Hexane to give 11.78 g (38%) of the title compound as a yellow solid.

$^1$H NMR (CDCl$_3$ 400 MHz) δ=2.69 (3H, s) 4.54 (2H, s) 7.20 (1H, s) 7.40 (3H, m), 7.48 (2H, m), 7.93 (1H, br.s)

MS(DCI.NH$_3$):262 (MNH$_4^+$, 20%), 245 (MH$^+$, 53%), 220 (52%), 204 (100%), 203 (100%)

| Microanalysis | C | H | N |
|---|---|---|---|
| Calc | 63.93 | 4.95 | 11.47 |
| Found | 64.11 | 5.02 | 11.41 |
|  | 64.05 | 4.90 | 11.44 |

REFERENCE EXAMPLE 2

Preparation of 4-(2-Dimethylaminoethylthio) benzaldehyde (5127)

2-dimethylaminoethanethiol hydrochloride (1.00 g, 7.06 mmol) was suspended in dry DMSO (20 ml) and sodium hydride (60% in mineral oil, 593 mg, 2.1 equivs) was added. The reaction mixture was left stirring for 40 mins to form Me$_2$NCH$_2$CH$_2$SNa, before 4-bromobenzaldehyde (1.193 g, 1 eq) was added, and the reaction mixture was then warmed to 90° C. under nitrogen. After 1 hour at 90°–100° C. analysis by thin layer chromatography (tlc) indicated almost complete disappearance of the starting material. The reaction mixture was therefore cooled, ethyl acetate was added and the mixture washed with sodium carbonate solution and brine. The mixture was then extracted with HCl (2N), basified and re-extracted with dichloromethane, dried over magnesium sulphate and the solvent was removed in vacuo to give the title compound as a yellow oil (73%).

REFERENCE EXAMPLE 3

Preparation of 5-(2-Dimethylaminoethylthio)-2-thiophenecarboxaldehyde 2-dimethylaminoethanethiol hydrochloride (1.85 g, 13.09 mmol) was suspended in dry DMSO and sodium hydride (60% dispersed in mineral oil, 1.10 g, 2.1 equivs) was added carefully. The reaction mixture was left stirring for 1 hour before 5-bromo-2-thiophenecarboxaldehyde (2.5 g, 1.56 ml, 13.09 mmol) was added. The reaction mixture was then heated to 90° C. under nitrogen.

After 3 hours the reaction mixture was cooled, diluted with ethyl acetate and washed with sodium carbonate (sat. soln, (3×)) before extracting with HCl (2N), basifying with sodium carbonate and reextracting with dichloromethane. The organic fraction was dried over magnesium sulphate and the solvent removed in vacuo to give the product as a brown oil (63% yield).

REFERENCE EXAMPLE 4

Preparation of 1-acetyl-3-(4-(2-dimethylaminoethylthio) benzylidene-2,5-piperazinedione A solution of 1,4-diacetyl-2,5-piperazinedione (2.27 g, 11.48 mmol) and 4-(2-dimethylaminoethylthio) benzaldehyde (4.01 g), prepared as in Reference Example 2, in dry THF (70 ml) was cooled to 0° C. Potassium t-butoxide in t-butanol (25 ml) was added dropwise over a period of 15 mins. When the addition was complete the mixture was warmed to room temperature slowly and then stirred at room temperature for 2.5 hours. Tlc (EtOAc:hexane, 1:1) showed that no starting material remained. The mixture was therefore diluted with ethyl acetate (150 ml) and washed with sodium carbonate. The organic phase was dried over magnesium sulphate and the solvent removed under vacuum. The resultant solid was then recrystallised from ethyl acetate and hexane and the resulting crystals filtered and dried.

REFERENCE EXAMPLE 5

Preparation of 4-(2-Dimethylaminoethylsulphinyl) benzaldehyde

Sodium periodate (512 mg, 2.39 mmol) was dissolved in water (10 ml) and cooled to 0° C. 4-(2-Dimethylaminoethylthio)benzaldehyde (0.5 g, 2.39 mmol), prepared as described in Reference Example 2, was then added in methanol (2 ml) and the reaction mixture stirred at room temperature and then later warmed to 35° C. After 7 hours the reaction mixture was basified using sodium carbonate and exhaustively extracted with dichloromethane, dried over magnesium sulphate and the solvent removed in vacuo to yield the title compound as an oil in a yield of 53%.

REFERENCE EXAMPLE 6

Preparation of 5-(6-Dimethylaminohexylthio)-2-thiophenecarboxaldehyde 6-dimethylaminohexanol was suspended in $CH_2Cl_2$ and treated with p-toluenesulphonic anhydride in the presence of triethylamine for 1 hour at 0° C. The reaction mixture was then treated with potassium thioacetate in DMF at 50° C. for a further hour. The resulting compound, $AcS(CH_2)_6NMe_2$, was treated with sodium carbonate in methanol at room temperature for 20 hours to give 6-(dimethylamino) hexanethiol. This was suspended in dry DMSO at room temperature and sodium hydride was added. The reaction mixture was left stirring for 30 mixtures. 5-bromo-2-thiophenecarboxaldehyde in DMSO was then added and the reaction mixture was warmed to 80° C. for 30 minutes to give the title compound. This is the starting aldehyde used in the preparation of compound 5442.

REFERENCE EXAMPLE 7

Preparation of 5-(2-dimethylaminoethylthio)-2-furancarboxaldehyde

2-Dimethylaminoethanethiol hydrochloride was suspended in dry DMSO and sodium hydride was added. The reaction mixture was left stirring for 40 minutes before 5-nitro-2-furancarboxaldehyde was added. The reaction mixture was allowed to stir for 30 minutes at room temperature, to give the title compound. This is the starting aldehyde used in the synthesis of compound 5253.

REFERENCE EXAMPLE 8

Preparation of 5-(2-dimethylaminoethylthio)-4-nitro-2-thiophenecarboxaldehyde

5-Bromo-2-thiophenecarboxaldehyde (8.1) was treated with $HNO_3$ and $H_2SO_4$ at −5° C. for 90 minutes to give compound 8.2 in 58% yield. Compound 8.2 was then treated with ethylene glycol, p-toluenesulphonic acid and toluene at reflux for 2 hours. Column chromatography of the reaction mixture gave compound 8.3 in 51% yield. This was then treated with $Me_2NCH_2CH_2SNa$, prepared as described in Reference Example 2, followed by HCl (2M) to give the title compound in 74% yield. This is the starting aldehyde used in the preparation of compound 5403.

REFERENCE EXAMPLE 9

Preparation of 4-(2-thiophenecarboxamido) benzaldehyde

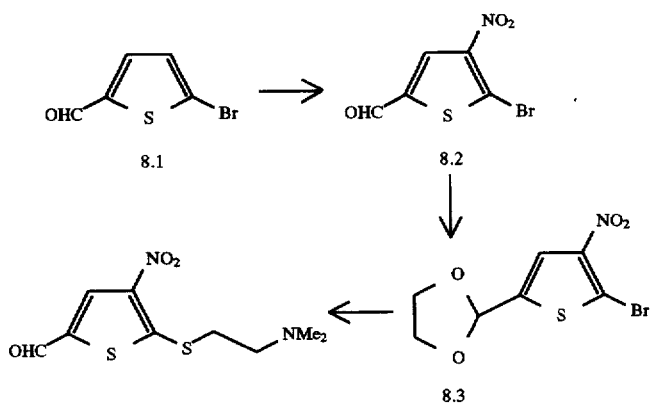

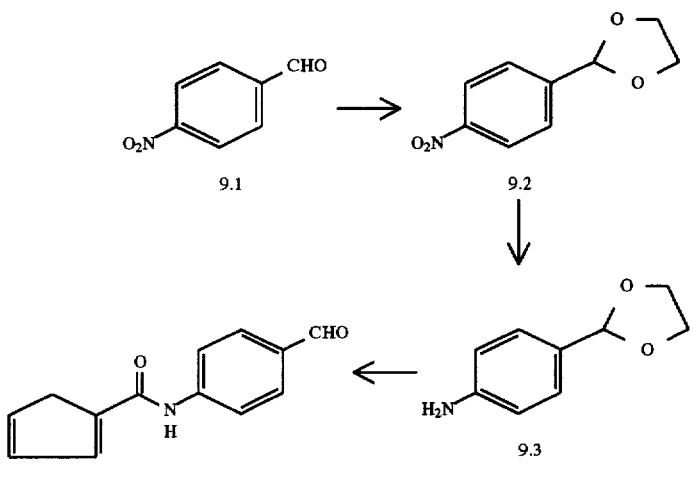

4-Nitrobenzaldehyde, compound 9.1, was treated with ethylene glycol and p-toluenesulphonic acid in toluene under reflux in a Dean and Stark apparatus. Compound 9.2 was obtained in 70% yield. The product was reduced by catalytic hydrogenation over a $PtO_2$ catalyst in ethanol to give compound 9.3, which was then treated with 2-thiophenecarbonyl chloride in $CH_2Cl_2$ in the presence of triethylamine at 0° C., with warming to room temperature. The product was recrystallised from EtOAc/hexane and then treated with HCl (1M) and THF to give the title compound in 60% yield. This is the starting aldehyde used in the preparation of compound 5507.

REFERENCE EXAMPLE 10

Preparation of 5-(2-diisopropylamineethyl)-2-thiophenecarboxaldehyde 2-(Diisopropylamino)ethanethiol hydrochloride was treated with sodium hydride in DMSO at room temperature for 1 hour. 5-Bromo-2-thiophenecarboxaldehyde in DMSO was then added and the reaction mixture was maintained at room temperature for 3 hours. The title compound was obtained in 36% yield. This is the starting aldehyde used in the preparation of compound 5399.

REFERENCE EXAMPLE 11

Preparation of Compounds of Formula (IV)

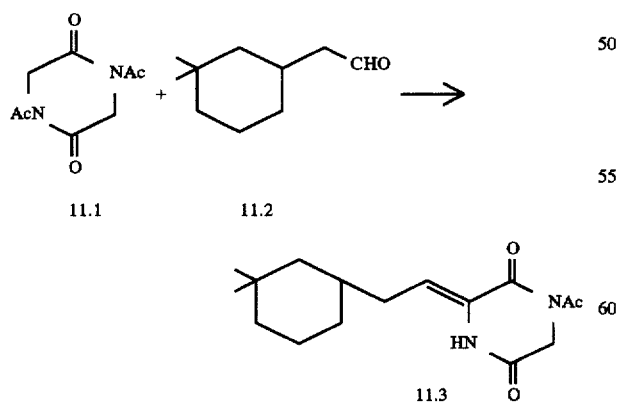

1,4-Diacetyl-2,5-piperazinedione, compound 11.1, was treated with the aldehyde 11.2 in THF in the presence of potassium t-butoxide/t-butanol at 0° C. The reaction mixture was warmed to room temperature over 16 hours to give compound 11.3, which is used in the preparation of compound 5455.

By replacing 11.2 with the appropriately substituted aldehyde, compounds of formula (IV) as defined earlier can be prepared in which X is a cyclohexyl or isopropyl group. These are starting compounds in the preparation of, respectively, compounds 5454 and 5448.

EXAMPLE 1

Preparation of 5128

1-acetyl-3-benzylidene-2,5-piperazinedione (1.141 g, 4.68 mmol), prepared as described in Reference Example 1, and caesium carbonate (1.523 g, 1 eq) were suspended in dry dimethylformamide (DMF). 4-(2-Dimethylaminoethylthio)-benzaldehyde (1.125 g, 1.1 eq), prepared as described in Reference Example 2, was then added. The reaction mixture was heated to 90° C. After 1 hour water was added and the mixture was stirred overnight. The mixture was then filtered and the solid collected and recrystallised from methanol/dichloromethane to yield the product as a pale yellow solid (62%).

EXAMPLE 2

Preparation of 5129

1-acetyl-3-(3-furylmethylene)-2,5-piperazinedione (1.0 g, 4.27 mmol) was dissolved in dry DMF (10 ml) and caesium carbonate (1.39 g, 1 eq) and 5127 (893 mg, 1 eq), prepared as described in Reference Example 2, were added. The reaction mixture was then heated to 90° C. with stirring. After 2 hours the reaction mixture was cooled, water added and the resulting solid collected by filtration and recrystallised from methanol/dichloromethane. The product was obtained as a yellow solid (17%).

EXAMPLE 3

Preparation of 5131

1-acetyl-3-benzylidene 2,5-piperazinedione (500 mg, 2.05 mmol), prepared as described in Reference Example 1, was dissolved in dry DMF (4 ml) and 5-(2-dimethylaminoethylthio)-2-thiophenecarboxaldehyde (485 mg, 1.1 eq), prepared as described in Reference Example 3, was added together with caesium carbonate (668 mg, 1 eq). The reaction mixture was heated to 90° C. After 1 hour, analysis by tlc showed there was no starting material present. The reaction mixture was therefore cooled, water was added and the precipitate collected by filtration. This was then recrystallised from methanol/dichloromethane to yield the title compound as a yellow solid (53%).

EXAMPLE 4

Preparation of 5133

The product of Reference Example 4 (1 g, 3.1 mmol) was heated to 90° C. with caesium carbonate (1.01 g, 1 eq) and thiophene-3-carboxaldehyde (0.35 g, 1 eq). After 3 hours the mixture was cooled to room temperature and water was added. The solid which formed was filtered and washed with water, methanol and diethylether. The solid was recrystallised from methanol/dichloromethane and the resulting crystals filtered and dried to give 0.458 g of the title compound (37.09% yield).

EXAMPLE 5

Preparation of 5141

1-acetyl-3-benzylidene-2,5-piperazinedione (260 mg, 1.07 mmol) was dissolved in dry DMF (2 ml) and caesium carbonate (34.8 mg, 1 eq) together with 4-(2-dimethylaminoethylsulphinyl)benzaldehyde (240 mg, 1 eq), prepared as in Reference Example 5, were added. The reaction mixture was heated at 80° C. for 2 hours and the reaction mixture was then cooled and water added. The precipitate produced was collected by filtration and recrystallised from methanol/dichloromethane. The title compound was obtained in 30% yield.

EXAMPLE 6

Preparation of Salts

5128.HCl, the salt with hydrochloric acid of 5128, was prepared as follows. 5128 (300 mg, 0.76 mmol) was dissolved in dry THF(200 ml) and anhydrous hydrogen chloride gas was bubbled through the solution. The solvent was removed in vacuo and the resulting solid recrystallised from methanol. The salt was obtained in 78% yield.

By the same procedure 5129.HCl was obtained from 5129 in 73% yield, 5131.HCl was obtained from 5131 in 76% yield, 5133.HCl was obtained from 5133 in 62% yield, and 5141.HCl was obtained from 5141.

EXAMPLE 7

Testing of the Present Compounds as PAI Inhibitors

The present compounds were tested in a PAI chromogenic substrate assay. In the assay (K. Nilsson, Fibrinolysis (1987) 1, 163–168) each compound was incubated with PAI-1 prior to addition to the tPA assay system. Inhibition of PAI-1 by the compounds of formula (I) resulted in the production of plasmin from plasminogen. In turn, the plasmin cleaved the chromogenic substrate S2251 (Kabi-Vitrum) producing pNA (p-nitroaniline) which was detected spectrophotometrically at 405 nm.

The degrees of inhibition observed in the chromogenic substrate assay at various concentrations, or the $IC_{50}$ values, for each compound are presented in Table 1.

TABLE 1

| Compound | % Inhibition | | | $IC_{50}$ μm |
|---|---|---|---|---|
| | 100 μm | 20 μm | 5 μm | |
| 5128.HCl | 69 | 71 | 5 | 10.0 |
| 5129.HCl | 50 | 68 | 51 | 4.5 |
| 5141.HCl | 34 | 6 | 0 | |
| 5133.HCl | 24 | 66 | | 3.0 |
| 5284 | | | | 3.0 |
| 5284.HCl | | | | 3.0 |
| 5292 | | | | 3.0 |
| 5294 | | | | 2.5 |
| 5292.HCl | | | | 2.0 |
| 5294.HCl | | | | 10.0 |
| 5131.HCl | 56 | 65 | | 5.0 |
| 5257 | 41 | 77 | | 7.0 |
| 5279 | 68 | 64 | | 20.0 |
| 5280 | 99 | 82 | | 20.0 |
| 5286 | 98 | 87 | | 8.0 |
| 5300.HCl | 26 | 41 | 10 | |
| 5286.HCl | 98 | 77 | | 14.0 |
| 5291 | | | | 20.0 |
| 5293 | | | | 20.0 |
| 5291.HCl | | | | 20.0 |
| 5293.HCl | | | | 20.0 |
| 5300 | 70 | 64 | | 25.0 |
| 5301 | 107 | 65 | | 20.0 |
| 5307 | 88 | 83 | | 8.5 |
| 5308 | 80 | 81 | | 4.7 |
| 5307.HCl | | | | 18.0 |
| 5308.HCl | 93 | 93 | | 4.5 |
| 5311 | | | | 15.0 |
| 5279.HCl | | | | 13.0 |
| 5313 | | 10 | | |
| 5314 | | | | 3.50 |
| 5315 | | | | 20.0 |
| 5316 | | 10 | | |
| 5313.HCl | | | | 20.0 |
| 5314.HCl | | | | 9.5 |
| 5315.HCl | | 10 | | |
| 5316.HCl | | 10 | | |
| 5280.HCl | | 20 | | |
| 5311.HCl | | | | 20.0 |
| 5399 | | 43 | 23 | |
| 5399.HCl | | 31 | 18 | |
| 5400 | | 60 | 61 | 4.50 |
| 5422 | | 21 | 3 | |
| 5422.HCl | | 28 | 5 | |
| 5423 | | 11 | 2 | |
| 5423.HCl | | 35 | 2 | 20.0 |
| 5424 | | 23 | 6 | 13.70 |
| 5424.HCl | | 45 | 8 | 15.70 |
| 5425 | | 57 | 37 | 3.70 |
| 5425.HCl | | 47 | 56 | 2.20 |
| 5426 | | 52 | 25 | 5.70 |
| 5426.HCl | | 55 | 35 | 5.40 |
| 5437 | | 41 | 8 | 20.00 |
| 5437.HCl | | 44 | 18 | 16.50 |
| 5438 | | 18 | 3 | |
| 5438.HCl | | 20 | 3 | |
| 5439 | | 46 | 5 | 15.0 |
| 5439.HCl | | 35 | 6 | 17.0 |
| 5440 | | 30 | 11 | |
| 5440.HCl | | 36 | 20 | |
| 5461 | | 44 | 1 | |
| 5461.HCl | | 56 | 10 | |
| 5462 | | 43 | 41 | |
| 5462.HCl | | 41 | 45 | |
| 5463 | | 78 | 76 | 4.0 |
| 5463.HCl | | 80 | 78 | 3.10 |
| 5465 | | 73 | 32 | 3.60 |
| 5465.HCl | | 76 | 42 | 2.60 |
| 5403 | | 52 | 26 | 20.0 |
| 5403.HCl | | 60 | 12 | |
| 5448 | | 0 | 0 | |
| 5454 | | 75 | 47 | 5.5 |
| 5454.HCl | | 69 | 25 | 5.3 |
| 5455 | | 59 | 30 | 6.5 |
| 5460 | | 83 | 34 | 12.2 |

TABLE 1-continued

| Compound | % Inhibition 100 μm | % Inhibition 20 μm | % Inhibition 5 μm | IC$_{50}$ μm |
|---|---|---|---|---|
| 5460.HCl | | 78 | 31 | 12.6 |
| 5464 | | 58 | 19 | 10.5 |
| 5464.HCl | | 61 | 17 | 11.2 |
| 5470 | | 0 | 1 | |
| 5470.HCl | | 1 | 1 | |
| 5471 | | 1 | 0 | |
| 5471.HCl | | 2 | 1 | |
| 5472 | | 22 | 0 | |
| 5473 | | 61 | 25 | 13.8 |
| 5473.HCl | | 54 | 10 | 20.0 |
| 5477 | | 59 | 10 | 20 |
| 5477.HCl | | 69 | 19 | 15.4 |
| 5482 | | 50 | 12 | 20 |
| 5482.HCl | | 59 | 13 | 20 |
| 5487 | | 60 | 15 | 8.6 |
| 5487.HCl | | 54 | 7 | 7.2 |
| 5488 | | 64 | 14 | 8.2 |
| 5488.HCl | | 60 | 15 | 7.6 |
| 5489 | | 56 | 6 | 13.6 |
| 5489.HCl | | 55 | 9 | 12.6 |
| 5497 | | 72 | 17 | 11.0 |
| 5497.HCl | | 59 | 12 | 11.5 |
| 5498 | | 52 | 15 | 20 |
| 5498.HCl | | 71 | 19 | 11.5 |
| 5476 | | 38 | 21 | |
| 5476.HCl | | 34 | 11 | |
| 5478.HCl | | 60 | 3 | 16.9 |
| 5479 | | 70 | 66 | 4.3 |
| 5479.HCl | | 75 | 62 | 4.8 |
| 5480 | | 74 | 53 | 5.2 |
| 5480.HCl | | 76 | 52 | 5.2 |
| 5481 | | 56 | 9 | 20 |
| 5481.HCl | | 55 | 10 | 20 |
| 5486 | | 55 | 13 | 20 |
| 5486.HCl | | 49 | 4 | 20 |
| 5490 | | 48 | 6 | 20 |
| 5490.HCl | | 66 | 12 | 10.8 |
| 5491 | | 65 | 0 | 14.2 |
| 5491.HCl | | 47 | 0 | 20 |
| 5499 | | 61 | 2 | 11.8 |
| 5499.HCl | | 54 | 0 | 18.4 |
| 5502 | | 12 | 0 | >20 |
| 5502.HCl | | 32 | 0 | >20 |

EXAMPLE 8

Pharmaceutical Composition

Tablets, each weighing 0.15 g and containing 25 mg of a compound of the invention can be manufactured as follows:

Composition for 10,000 tablets: compound of the invention (250 g); lactose (800 g); corn starch (415 g); talc powder (30 g); magnesium stearate (5 g).

The compound of the invention, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium stearate is added, carefully mixed and processed into tablets.

EXAMPLE 9

Characterisation of the Present Compounds

The compounds and salts prepared in the preceding Examples were characterised by mass spectroscopic, microanalytical and proton NMR techniques. The results are set out in Table 2:

| No. | Mol. Formula | Mass spec data Mass (intensity) | mode | $^1$H nmr data solvent/field | δ |
|---|---|---|---|---|---|
| 5129 | $C_{20}H_{21}N_3O_3S$ | 384 (20), 311 (100) | ESI | CDCl$_3$/400 MHz | 2.32 (6H, s), 2.55 (2H, t), 3.10 (2H, t), 6.60 (1H, s), 6.83 (1H, s), 6.97 (1H, s), 7.32 (2H, d), 7.38 (2H, d), 7.56 (1H, s), 7.70 (1H, s), 7.82 (1H, brs), 8.06 (1H, brs) |
| 5131 | $C_{20}H_{21}N_3O_2S_2$ | 400 (100), 234 (10), 219 (10) | ESI | d$_6$-DMSO/400 MHz | 2.17 (6H, s), 2.50 (2H, t), 3.01 (2H, t), 6.78 (1H, s), 6.86 (1H, s), 7.19 (1H, d), 7.31–7.55 (6H, m), 10.2 (2H, br) |
| 5133 | $C_{20}H_{21}N_3O_2S_2$ | 400 (100) | ESI | d$_6$-DMSO/400 MHz | 2.20 (6H, s), 2.50 (2H, t), 3.11 (2H, t), 6.75 (1H, s), 6.85 (1H, s), 7.35 (2H, d), 7.41 (1H, m), 7.50 (2H, d), 7.61 (1H, m), 7.95 (1H, m), 10.15 (2H, br) |
| 5141 | $C_{22}H_{23}N_3O_3S$ | 410 (100) | ESI | d$_6$-DMSO/400 MHz | 2.18 (6H, s), 2.30–2.40 (1H, m), 2.65–2.75 (1H, m), 2.77–2.87 (1H, m), 3.02–3.12 (1H, m), 6.80 (1H, s), 6.82 (1H, s), 7.30–7.37 (1H, m), 7.40–7.47 (2H, m), 7.55 (2H, d), 7.65–7.75 (4H, m), 10.30 (2H, brs) |
| 5284 | $C_{26}H_{25}N_3O_2S$ | | | CDCl$_3$/400 MHz | 2.30 (6H, s), 2.62 (2H, t), 3.10 (2H, t), 7.00 (1H, s), 7.17 (1H, s), 7.33 (2H, d), 7.40 (2H, d), 7.45–7.48 (1H, m), 7.54–7.57 (2H, m), 7.85–7.95 (4H, m), 8.12 (1H, brs), 8.30 (1H, brs) |
| 5284.HCl | $C_{26}H_{25}N_3O_2S$·HCl | 444 (100) | DCI (NH$_3$) | d$_6$-DMSO/400 MHz | 2.82 (6H, s), 3.30 (2H, t), 3.39 (2H, t), 6.80 (1H, s), 6.95 (1H, s), 7.44 (2H, d), 7.52–7.65 (5H, m), 7.88–7.95 (3H, m), 8.10 (1H, s), 10.25 (2H, brs), 10.45 (1H, brs) |
| 5128.HCl | $C_{22}H_{23}N_3O_2S$·HCl | 394 (45), 321 (100) | ESI | d$_6$-DMSO/400 MHz | 2.78 (6H, s), 3.22 (2H, m), 3.48 (2H, m), 6.77 (1H, s), 6.80 (1H, s), 7.30–7.55 (9H, m), 10.26 (1H, s), 10.28 (1H, s), 10.55 (1H, brs) |
| 5129.HCl | $C_{20}H_{21}N_3O_3S$·HCl | 384 (100) | CI | d$_6$-DMSO/400 MHz | 2.78 (6H, s), 3.25 (2H, m), 3.40 (2H, m), 6.70 (1H, s), 6.76 (1H, s), 6.95 (1H, s), 7.45 (2H, d), 7.55 (2H, d), 7.76 (1H, s), 8.23 (1H, s), 9.86 (1H, s), 10.18 (1H, s), 10.28 (1H, brs) |
| 5141.HCl | $C_{22}H_{23}N_3O_3S$·HCl | 410 (100) | DCI | d$_6$-DMSO/400 MHz | 2.78 (6H, s), 3.18 (1H, m), 3.30 (1H, m), 3.45 (1H, m), 3.56 (1H, m), 6.80 (1H, s), 6.84 (1H, s), 7.34 (1H, m), 7.47 (2H, m), 7.55 (2H, d), 7.78 (2H, d), 10.30 (1H, br), |

| | | | | | |
|---|---|---|---|---|---|
| 5133.HCl | $C_{20}H_{21}N_3O_2S_2$.HCl | | | $d_6$-DMSO/400 MHz | 10.35 (1H, s), 10.45 (1H, s) 2.80 (6H, s), 3.25 (2H, m), 3.41 (2H, m), 6.78 (1H, s), 6.85 (1H, s), 7.40 (1H, m), 7.45 (2H, d), 7.55 (2H, d), 7.62 (1H, m), 7.99 (1H, m), 10.03 (1H, s), 10.22 (1H, s), 10.50 (1H, br) |
| 5131.HCl | $C_{20}H_{21}N_3O_2S_2$.HCl | 400 (100) | ESI | $d_6$-DMSO/400 MHz | 2.78 (6H, s), 3.25 (4H, s), 6.70 (1H, s), 6.89 (1H, s), 7.32–7.55 (7H, m), 9.90 (1H, s), 10.13 (1H, brs), 10.32 (1H, s) |
| 5286.HCl | $C_{24}H_{23}N_3O_2S$.HCl | 450 (10) | DCI | $d_6$-DMSO/400 MHz | 2.73 (6H, s), 3.20–3.30 (4H, m), 6.90 (1H, s), 6.95 (1H, s), s), 7.32 (1H, d), 7.47–7.55 (3H, m), 7.62 (1H, d), 7.88–7.98 (3H, m), 8.12 (1H, s), 10.00 (1H, brs), 10.50 (1H, brs) |
| 5291 | $C_{20}H_{20}ClN_3O_2S_2$ | 434 (35) | DCI (NH$_3$) | $d_6$-DMSO/400 MHz | 2.15 (6H, s), 2.50 (2H, t), 3.01 (2H, t), 6.71 (1H, s), 6.85 (1H, s), 7.15 (1H, d), 7.35–7.47 (4H, m), 7.57 (1H, s) |
| 5292 | $C_{22}H_{22}ClN_3O_2S$ | 428 (100) | DCI (NH$_3$) | $d_6$-DMSO/400 MHz | 2.15 (6H, s), 2.50 (2H, t), 3.05 (2H, t), 6.70 (1H, s), 6.73 (1H, s), 7.30–7.50 (7H, m), 7.60 (1H, s), 10.30 (1H, brs) |
| 5293 | $C_{21}H_{20}F_3N_3O_2S_2$ | 468 (100) | DCI (NH$_3$) | $d_6$-DMSO/400 MHz | 2.15 (6H, s), 2.50 (2H, t), 3.01 (2H, t), 6.80 (1H, s), 6.85 (1H, s), 7.15 (1H, d) 7.40 (1H, d), 7.70–7.75 (4H, m), 10.35 (1H, brs) |
| 5294 | $C_{23}H_{22}F_3N_3O_2S$ | 462 (10) | DCI (NH$_3$) | $d_6$-DMSO/400 MHz | 2.18 (6H, s), 2.50 (2H, t), 3.10 (2H, t), 6.75 (1H, s), 6.79 (1H, s), 7.32 (2H, d), 7.50 (2H, d), 7.70–7.72 (4H, m), 10.37 (2H, brs) |
| 5291.HCl | $C_{20}H_{20}ClN_3O_2S_2$.HCl | 434 (15) | DCI (NH$_3$) | $d_6$-DMSO/400 MHz | 2.75 (6H, s), 3.20–3.31 (4H, m), 6.75 (1H, s), 6.90 (1H, s), 7.35–7.50 (5H, m), 7.60 (1H, s), 9.95 (1H, brs), 10.55 (1H, brs), 10.80 (1H, brs) |
| 5292.HCl | $C_{22}H_{22}ClN_3O_2S$.HCl | 428 (20) | DCI | $d_6$-DMSO/400 MHz | 2.80 (6H, s), 3.22 (2H, t), 3.42 (2H, t), 6.72 (1H, s), 6.75 (1H, s), 7.35–7.58 (8H, m), 10.35 (1H, brs), 10.50 (1H, brs), 10.70 (1H, brs) |
| 5293.HCl | $C_{21}H_{20}F_3N_3O_2S_2$.HCl | 468 (25) | DCI (NH$_3$) | $d_6$-DMSO/400 MHz | 2.75 (6H, s), 3.22–3.30 (4H, m), 6.80 (1H, s), 6.90 (1H, s), 7.35 (1H, d), 7.45 (1H, d), 7.68–7.45 (4H, m), 10.00 (1H, brs), 10.55 (1H, brs), 10.75 (1H, brs) |
| 5294.HCl | $C_{23}H_{22}F_3N_3O_2S$.HCl | 462 (10) | DCI | $d_6$-DMSO/400 MHz | 2.75 (6H, s), 3.20 (2H, t), 3.45 (2H, t), 6.75 (1H, s), 6.79 (1H, s), 7.45 (2H, d), 7.55 (2H, d), 7.70–7.75 (4H, m), 10.35 (1H, brs), 10.50 (1H, brs) |
| 5307 | $C_{23}H_{22}N_4O_2S_2$ | | | $d_6$-DMSO/400 MHz | 2.17 (6H, s), 2.54 (2H, t), 3.05 (2H, t), 6.88 (1H, s), 7.15 (1H, s), 7.20 (1H, d), 7.45 (1H, d), 7.55 (1H, d), 7.62–7.80 (2H, m), 7.95 (1H, d), 8.05 (1H, d), 8.88 (1H, d) |
| 5308 | $C_{23}H_{22}N_4O_2S_2$ | | | $d_6$-DMSO/400 MHz | 2.18 (6H, s), 2.55 (2H, t), 3.05 (2H, t), 6.85 (1H, s), 6.95 (1H, s), 7.18 (1H, d), 7.50 (1H, d), 7.50–7.55, (1H, m), 7.65 (1H, d), 7.82–7.86 (1H, m), 8.00 (2H, d), 8.45 (1H, d), 13.15 (1H, brs) |
| 5307.HCl | $C_{23}H_{22}N_4O_2S_2$.HCl | 451 (20) | DCI (NH$_3$) | $d_6$-DMSO/400 MHz | 2.75 (6H, s), 3.25 (4H, m), 6.92 (1H, s), 7.20 (1H, s), 7.35 (1H, d), 7.50 (1H, d), 7.79–7.90 (2H, m), 8.00–8.05 (1H, m), 8.15 (1H, d), 8.38 (1H, d), 9.10 (1H, d), 10.15 (1H, brs), 10.54 (1H, brs), 10.60 (1H, brs) |
| 5308.HCl | $C_{23}H_{22}N_4O_2S_2$.HCl | 451 (5) | DCI (NH$_3$) | $d_6$-DMSO/400 MHz | 2.54 (6H, s), 3.00 (2H, t), 3.19 (2H, t), 6.85 (1H, s), 6.98 (1H, s), 7.30 (1H, d), 7.54 (1H, d), 7.62–7.66 (1H, m), 7.78 (1H, d), 7.83–7.87 (1H, m), 7.98–8.02 (2H, m), 8.45 (1H, d), 13.18 (1H, brs) |
| 5311 | $C_{22}H_{23}N_3O_3S_2$ | | | $d_6$-DMSO/400 MHz | 2.15 (6H, s), 2.48 (2H, t), 3.00 (2H, t), 3.20 (2H, t), 4.55 (2H, t), 6.75 (1H, s), 6.80 (1H, d), 6.85 (1H, s), 7.15 (1H, d), 7.30 (1H, d), 7.40 (1H, d), 7.48 (1H, s), 10.10 (1H, brs) |
| 5337 | $C_{22}H_{23}N_3O_3S_2$.HCl | 442 (100) | ESI | $d_6$-DMSO/400 MHz | 2.75 (6H, s), 3.20 (2H, t), 3.25–3.30 (4H, m), 4.55 (2H, t), 6.75 (1H, s), 6.80 (1H, d), 6.85 (1H, s), 7.25–7.30 (2H, m), 7.43–7.47 (2H, m), 9.75 (1H, brs), 10.15 (1H, brs), 10.50 (1H, brs) |
| 5399 | $C_{24}H_{29}N_3O_2S_2$ | 456 (100), 128 (100) | DCI (NH$_3$) | $d_6$-DMSO/400 MHz | 0.96 (12H, d), 2.69 (2H, t), 2.90–3.00 (4H, m), 6.80 (1H, s), 6.88 (1H, s), 7.18 (1H, d), 7.30–7.35 (1H, m), 7.39–7.44 (3H, m), 7.55 (2H, d), 10.10 (1H, brs) |
| 5400 | $C_{22}H_{22}N_4O_4S$ | 439 (100) | ESI | CDCl$_3$+CF$_3$CO$_2$D/ 400 MHz | 3.07 (6H, s), 3.42–3.49 (2H, m), 3.59–3.53 (2H, m), 7.20 (1H, s), 7.35 (1H, s), 7.45–7.55 (6H, m), 7.66–7.70 (1H, m), 8.25 (1H, brs) |
| 5400.HCl | $C_{22}H_{22}N_4O_4S$.HCl | 439 (100) | ESI | $d_6$-DMSO/400 MHz | 2.85 (6H, s), 3.30–3.37 (2H, m), 3.50–3.57 (2H, m), 6.82 (1H, s), 6.83 (1H, s), 7.32–7.37 (1H, m), 7.44 (2H, t), 7.53 (2H, d), 7.79–7.89 (2H, m), 8.34 (1H, s), 10.30 (1H, brs), 10.55 (1H, brs), 10.69 (1H, brs) |
| 5403.HCl | $C_{20}H_{20}N_4O_4S_2$.HCl | 445 (100) | DCI (NH$_3$) | $d_6$-DMSO/400 MHz | 2.82 (6H, s), 3.45 (2H, t), 3.58 (2H, t), 6.80 (1H, s), 6.82 (1H, s), 7.35 (1H, m), 7.42 (2H, m), 7.55 (2H, d), 8.06 (1H, s), 10.33 (1H, brs), 10.65 (2H, br) |
| 5422 | $C_{22}H_{22}N_4O_4S$ | 439 (80) | FAB (+) | $d_6$-DMSO/300 MHz | 2.29 (6H, s), 2.50 (2H, t), 3.23 (2H, t), 6.86 (1H, s), 6.92 (1H, s), 7.44 (2H, d), 7.61 (2H, d), 7.77 (1H, t), 8.03 (1H, d), 8.23 (1H, d), 8.48 (1H, s), 10.50–11.00 (2H, br) |
| 5423 | $C_{23}H_{22}F_3N_3O_2S$ | 462 (90), 389 (50) | FAB (+) | $d_6$-DMSO/300 MHz | 2.20 (6H, s), 2.50 (2H, t), 3.14 (2H, t), 6.77 (1H, s), 6.84 (1H, s), 7.34 (2H, d), 7.52 (2H, d), 7.66 (2H, m), 7.78–7.87 (2H, m), 10.40–10.70 (2H, br) |
| 5425 | $C_{22}H_{22}BrN_3O_2S$ | 474 (50), 472 (50), 439 (10), 401 (10), 399 (10), 286 (50), 132 (100) | FAB (+) | $d_6$-DMSO/200 MHz | 2.19 (6H, s), 2.50 (2H, t), 3.13 (2H, t), 6.71 (1H, s), 6.74 (1H, s), 7.32–7.40 (3H, m), 7.50–7.54 (4H, m), 7.79 (1H, s), 10.40–10.60 (2H, br) |
| 5425.HCl | $C_{22}H_{22}BrN_3O_2S$.HCl | 474 (90), 472 (85), 391 (40), | FAB (+) | $d_6$-DMSO/300 MHz | 2.79 (6H, s), 3.21–3.30 (2H, m), 3.37–3.45 (2H, m), 6.72 (1H, s), 8.77 (1H, s), 7.36 (1H, t), 7.43–7.56 (6H, m), 7.72 |

| | | | | | |
|---|---|---|---|---|---|
| 5428 | $C_{20}H_{20}N_4O_4S_2$ | 149 (50)<br>445 (100), 372 (15), 286 (65) | FAB (+) | $d_6$-DMSO/200 MHz | (1H, s), 10.39 (1H, s), 10.51 (1H, br), 10.62 (1H, s)<br>2.18 (6H, s), 2.50 (2H, t), 3.05 (2H, t), 6.83 (1H, s), 6.91 (1H, s), 7.20 (1H, d), 7.44 (1H, d), 7.80 (2H, d), 8.24 (2H, d) |
| 5429 | $C_{21}H_{23}N_3O_2S_3$ | 446 (100), 373 (10), 286 (15), 149 (30), 132 (30) | FAB (+) | $d_6$-DMSO/200 MHz | 2.17 (6H, s), 2.50 (2H, t), 3.04 (2H, t), 6.76 (1H, s), 6.88 (1H, s), 7.19 (1H, d), 7.30 (2H, d), 7.43 (1H, d), 7.51 (2H, d), 10.1–10.6 (2H, br) |
| 5431 | $C_{21}H_{20}N_4O_2S_2$ | 425 (100), 307 (10), 286 (20) | FAB (+) | $d_6$-DMSO/200 MHz | 2.18 (6H, s), 2.50 (2H, t), 3.05 (2H, t), 6.79 (1H, s), 6.90 (1H, s), 7.20 (1H, d), 7.44 (1H, d), 7.71 (2H, d), 7.87 (2H, d) |
| 5433.HCl | $C_{20}H_{20}BrN_3O_2S_2$.HCl | 480 (50), 478 (40), 96 (100) | CI | $d_6$-DMSO/300 MHz | 2.85 (6H, s), 3.36 (4H, s), 6.84 (1H, s), 7.01 (1H, s), 7.46 (2H, m), 7.60 (3H, m), 7.82 (1H, s), 10.19 (1H, s), 10.67 (1H, s), 10.78 (1H, s) |
| 5434.HCl | $C_{21}H_{20}N_4O_2S_2$.HCl | 425 (60), 106 (30), 72 (100) | CI | $d_6$-DMSO/300 MHz | 2.86 (6H, s), 3.36 (4H, s), 6.88 (1H, s), 7.02 (1H, s), 7.44 (1H, d), 7.60 (1H, d), 7.69 (1H, m), 7.89 (2H, m), 8.10 (1H, s), 10.19 (1H, s), 10.50 (1H, s), 10.88 (1H, s) |
| 5437 | $C_{22}H_{22}ClN_3O_2S$ | 428 (100), 355 (10) | FAB (+) | $d_6$-DMSO/200 MHz | 2.20 (6H, s), 2.50 (2H, t), 3.13 (2H, t), 6.76 (2H, s), 7.35 (2H, d), 7.46–7.60 (6H, m), 10.28–10.53 (2H, br) |
| 5438 | $C_{23}H_{25}N_3O_3S$ | 424 (100), 351 (20) | FAB (+) | $d_6$-DMSO/200 MHz | 2.20 (6H, s), 2.50 (2H, t), 3.13 (2H, t), 3.81 (3H, s), 6.76 (1H, s), 6.77 (1H, s), 6.92 (1H, m), 7.13 (2H, m), 7.31–7.39 (3H, m), 7.52 (2H, d), 10.34 (2H, br) |
| 5439 | $C_{23}H_{25}N_3O_2S$ | 408 (100), 335 (85), 286 (75) | FAB (+) | $d_6$-DMSO/200 MHz | 2.19 (6H, s), 2.35 (3H, s), 2.50 (2H, t), 3.12 (2H, t), 6.70 (1H, s), 6.71 (1H, s), 7.14 (1H, m), 7.31–7.41 (5H, m), 7.56 (2H, d), 10.10–10.40 (2H, br) |
| 5439.HCl | $C_{23}H_{25}N_3O_2S$.HCl | 408 (100), 72 (50) | CI | $d_6$-DMSO/300 MHz | 2.89 (6H, s), 3.31–3.27 (2H, m), 3.52–3.58 (2H, m), 6.85 (1H, s), 6.87 (1H, s), 7.26 (1H, d), 7.41–7.43 (2H, m), 7.49 (1H, s), 7.56 (2H, d), 7.65 (2H, d), 10.42 (1H, s), 10.46 (1H, s), 10.89 (1H, brs) |
| 5442.HCl | $C_{24}H_{29}N_3O_2S_2$.HCl | 456 (100) | DCI ($NH_3$) | $d_6$-DMSO | 1.31 (2H, m), 1.42 (2H, m), 1.62 (4H, m), 2.72 (6H, s), 2.95 (2H, t), 2.98 (2H, t), 6.80 (1H, s), 6.89 (1H, s), 7.19 (1H, d), 7.34 (1H, m), 7.42 (3H, m), 7.55 (2H, d), 10.00 (2H, br), 10.25 (1H, brs) |
| 5448 | $C_{17}H_{23}N_3O_2S_2$ | 366 (20) | DCI ($NH_3$) | $d_6$-DMSO/400 MHz | 0.99 (6H, d), 2.15 (2H, s), 2.50 (2H, t), 2.95 (1H, m), 3.00 (2H, t), 5.73 (1H, d), 6.81 (1H, s), 7.16 (1H, d), 7.37 (1H, d), 10.30 (1H, brs) |
| 5454 | $C_{20}H_{27}N_3O_2S_2$ | 406 (5) | DCI ($NH_3$) | $d_6$-DMSO/400 MHz | 1.05–1.25 (3H, m), 1.25–1.39 (2H, m), 1.55–1.70 (5H, m), 2.15 (6H, s), 2.50 (2H, t), 2.60–2.75 (1H, m), 3.00 (2H, t), 5.71 (1H, d), 6.82 (1H, s), 7.16 (1H, d), 7.35 (1H, d), 10.35 (1H, brs) |
| 5455 | $C_{23}H_{33}N_3O_2S_2$ | 448 (25) | DCI | $d_6$-DMSO/400 MHz | 0.73–1.70 (15H, m including 0.85, 2×3H, s), 2.14 (2H, m), 2.50 (2H, t), 3.00 (2H, t), 5.90 (1H, t), 6.81 (1H, s), 71.7 (1H, d), 7.36 (1H, d), 10.27 (1H, s) |
| 5461 | $C_{22}H_{22}N_4O_4S$ | 439 (100), 366 (20), 286 (20), 132 (30) | FAB (+) | $d_6$-DMSO/200 MHz | 2.23 (6H, s), 2.50 (2H, t), 3.15 (2H, t), 6.79 (1H, s), 6.84 (1H, s), 7.36 (2H, d), 7.53 (2H, d), 7.81 (2H, d), 8.25 (2H, d) |
| 5461.HCl | $C_{22}H_{22}N_4O_4S$.HCl | 439 (10), 58 (100) | CI | $d_6$-DMSO/300 MHz | 2.78 (6H, s), 3.19–3.27 (2H, m), 3.38–3.45 (2H, m), 6.79 (1H, s), 6.83 (1H, s), 7.44 (2H, d), 7.55 (2H, d), 7.78 (2H, d), 8.23 (2H, d), 10.40–10.55 (2H, br), 10.70–10.80 (1H, br) |
| 5462 | $C_{23}H_{22}N_4O_2S$ | 419 (100), 346 (20) | FAB (+) | $d_6$-DMSO/200 MHz | 2.20 (6H, s), 2.50 (2H, t), 3.14 (2H, t), 6.78 (1H, s), 6.79 (1H, s), 7.36 (2H, d), 7.51 (2H, d), 7.72 (2H, d), 7.87 (2H, d), 10.40–10.60 (2H, br) |
| 5463 | $C_{23}H_{25}N_3O_2S$ | 408 (100), 335 (30) | FAB (+) | $d_6$-DMSO/200 MHz | 2.20 (6H, s), 2.35 (3H, s), 2.50 (2H, t), 3.13 (2H, t), 6.75 (1H, s), 6.76 (1H, s), 7.25 (2H, d), 7.35 (2H, d), 7.45–7.54 (4H, m), 10.15–10.35 (2H, br) |
| 5464.HCl | $C_{21}H_{23}N_3O_3S_2$.HCl | 430 (100), 72 (100) | CI | $d_6$-DMSO/300 MHz | 2.75 (6H, s), 3.26 (4H, s), 3.79 (3H, s), 6.77 (1H, s), 6.88 (1H, s), 6.98 (2H, d), 7.34 (1H, d), 7.48 (1H, d), 7.53 (2H, d), 9.85–9.95 (1H, br), 10.31 (1H, s), 10.50–10.65 (1H, br) |
| 5465 | $C_{22}H_{21}Cl_2N_3O_2S$ | 464 (80), 462 (100), 391 (30) | FAB (+) | $d_6$-DMSO/200 MHz | 2.20 (6H, s), 2.50 (2H, t), 3.13 (2H, t), 6.72 (1H, s), 6.77 (1H, s), 7.35 (2H, d), 7.49–7.53 (3H, m), 7.66 (1H, d), 7.81 (1H, d), 10.40–10.70 (2H, br) |
| 5470 | $C_{19}H_{20}N_4S_2O_2$ | 401 (8) | DCI ($NH_3$) | $d_6$-DMSO/400 MHz | 2.15 (6H, s), 2.50 (2H), 3.00 (2H, t), 6.74 (1H, s), 6.85 (1H, s), 7.15 (1H, d), 7.37–7.40 (2H, m), 7.90–7.95 (1H, m), 8.46–8.48 (1H, m), 8.67–8.68 (1H, m) |
| 5471 | $C_{19}H_{20}N_4S_2O_2$ | 401 (4) | CI | $d_6$-DMSO/400 MHz | 2.15 (6H, s), 2.50 (2H, t), 3.30 (2H, t), 6.72 (1H, s), 6.91 (1H, s), 7.16 (1H, d), 7.35–7.39 (1H, m), 7.45 (1H, d), 7.65 (1H, d), 7.90 (1H, t), 8.70 (1H, d), 12.5 (1H, brs) |
| 5471.HCl | $C_{19}H_{20}N_4S_2O_2$.HCl | | | $d_6$-DMSO/400 MHz | 2.74 (6H, s), 3.20–3.33 (4H, m), 6.74 (1H, s), 6.93 (1H, s), 7.29–7.38 (2H, m), 7.51 (1H, d), 7.67 (1H, d), 7.90 (1H, t), 8.72 (1H, d), 10.10 (1H, brs), 10.60 (1H, brs), 12.40 (1H, s) |
| 5472 | $C_{19}H_{20}N_4S_2O_2$ | 401 (37) | CI | $d_6$-DMSO/400 MHz | 2.29 (6H, s), 2.58 (2H, t), 3.05 (2H, t), 6.92 (1H, s), 7.06 (1H, s), 7.12–7.15 (2H, m), 7.25–7.30 (2H, m) 8.03–8.18 (1H, brs), 8.68–8.74 (2H, d) |
| 5473 | $C_{23}H_{24}N_4O_2S_2$ | 453 (27) | CI | $d_6$-DMSO/400 MHz | 2.17 (6H, s), 2.50 (2H, t), 30.2 (2H, t), 3.86 (3H, s), 6.85 (1H, s), 7.08 (1H, s), 7.15–7.18 (2H, m), 7.25 (1H, t), 7.43 (1H, d), 7.53 (1H, d), 7.72 (1H, d), 8.14 (1H, s), 9.70 (1H, brs) |

-continued

| Compound | Formula | MS | Method | NMR |
|---|---|---|---|---|
| 5473.HCl | C$_{23}$H$_{24}$N$_4$O$_2$S$_2$.HCl | | | d$_6$-DMSO/400 MHz 2.50 (2H, m), 2.76 (6H, s), 3.25 (2H, m), 3.87 (3H, s), 6.88 (1H, s), 7.12 (1H, s), 7.17 (1H, t), 7.27 (1H, t), 7.33 (1H, d), 7.48 (1H, d), 7.54 (1H, d), 7.71 (1H, d), 8.12 (1H, s), 9.62 (1H, brs), 9.77 (1H, brs), 9.98 (1H, brs) |
| 5476 | C$_{23}$H$_{22}$N$_4$O$_2$S | 419 (30), 286 (40), 149 (20) | FAB (+) | d$_6$-DMSO/200 MHz 2.19 (6H, s), 2.50 (2H, t), 3.13 (2H, t), 6.75 (1H, s), 6.76 (1H, s), 7.34 (2H, d), 7.52 (2H, d), 7.62 (1H, d), 7.77–7.86 (2H, m), 8.07 (1H, s), 10.30–10.75 (2H, br) |
| 5476.HCl | C$_{23}$H$_{22}$N$_4$O$_2$S.HCl | 419 (100), 72 (90) | CI | d$_6$-DMSO/300 MHz 2.79 (6H, s), 3.21–3.47 (2H, m), 3.41–3.46 (2H, m), 6.77 (1H, s), 6.79 (1H, s), 7.45 (2H, d), 7.54 (2H, d), 7.60 (1H, d), 7.75–7.81 (2H, m), 8.00 (1H, s), 10.44 (1H, s), 10.67–10.72 (2H, br) |
| 5477 | | 458 (100), 385 (20) | FAB (+) | d$_6$-DMSO/200 MHz 2.18 (6H, s), 2.50 (2H, t), 3.06 (2H, t), 3.89 (3H, s), 6.82 (1H, s), 6.91 (1H, s), 7.20 (1H, d), 7.45 (1H, d), 7.69 (2H, d), 7.98 (2H, d) |
| 5479 | C$_{23}$H$_{25}$N$_3$O$_3$S | 424 (100), 351 (55) | FAB (+) | d$_6$-DMSO/200 MHz 2.19 (6H, s), 2.50 (2H, t), 3.13 (2H, t), 3.81 (3H, s), 6.73 (1H, s), 6.76 (1H, s), 7.00 (2H, d), 7.34 (2H, d), 7.52 (4H, m), 10.25 (2H, brs) |
| 5481 | C$_{29}$H$_{29}$N$_3$O$_3$S | 500 (32), 72 (100) | CI (NH$_3$) | d$_6$-DMSO/300 MHz 2.20 (6H, s), 2.50 (2H, m), 3.15 (2H, m), 5.18 (2H, s), 6.73 (1H, s), 6.76 (1H, s), 7.08 (2H, d), 7.44 (11H, m), 10.25 (2H, brs) |
| 5482 | | 506 (22), 286 (30), 267 (47), 213 (45), 72 (100), | DCI (NH$_3$) | d$_6$-DMSO/200 MHz 2.17 (6H, s), 2.50 (2H, t), 3.05 (2H, t), 5.18 (2H, s), 6.75 (1H, s), 6.87 (1H, s), 7.08 (2H, d), 7.19 (1H, d), 7.46 (8H, m), 10.23 (2H, brs) |
| 5486 | C$_{29}$H$_{29}$N$_3$O$_3$S | 500 (61), 72 (100) | CI (NH$_3$) | d$_6$-DMSO/300 MHz 2.19 (6H, s), 2.50 (2H, t), 3.13 (2H, t), 5.17 (2H, s), 6.75 (2H, s), 6.96–7.54 (13H, m), 10.34 (2H, brs) |
| 5488 | C$_{28}$H$_{28}$N$_4$O$_6$S$_2$ | 581 (90), 508 (5), 446 (10), 242 (100) | FAB (+) | d$_6$-DMSO/200 MHz 2.19 (6H, s), 2.50 (2H, t), 3.05 (2H, t), 3.87 (3H, s), 5.34 (2H, s), 6.78 (1H, s), 6.88 (1H, s), 7.05–7.22 (4H, m), 7.44 (1H, d), 7.74 (2H, d), 8.29 (2H, d), 10.25–10.40 (2H, br) |
| 5488.HCl | C$_{28}$H$_{28}$N$_4$O$_6$S$_2$ | 581 (29), 446 (18), 244 (53), 106 (100) | DCI (NH$_3$) | d$_6$-DMSO/300 MHz 2.83 (6H, s), 3.34 (4H, brs), 3.95 (3H, s), 5.42 (2H, s), 6.86 (1H, s), 6.98 (1H, s), 7.15 (1H, d), 7.22 (1H, m), 7.29 (1H, d), 7.43 (1H, d), 7.58 (1H, d), 7.82 (2H, d), 8.38 (2H, d), 10.06 (1H, s), 10.50 (1H, s), 10.67 (1H, s) |
| 5489 | C$_{20}$H$_{20}$BrN$_3$O$_2$S$_2$ | 480 (100), 478 (90), 407 (20), 405 (15), 286 (10), 151 (20), 138 (30) | FAB (+) | d$_6$-DMSO/200 MHz 2.27 (6H, s), 2.55–2.70 (2H, m), 3.04–3.11 (2H, m), 6.75 (1H, s), 6.90 (1H, s), 7.22 (1H, d), 7.45–7.52 (3H, m), 7.62 (2H, d) |
| 5489.HCl | | 480 (100), 478 (92), 106 (65), 72 (100), 58 (51) | DCI (NH$_3$) | d$_6$-DMSO/300 MHz 2.80 (6H, s), 3.02 (4H, m), 6.84 (1H, s), 7.00 (1H, s), 7.42 (1H, d), 7.59 (3H, m), 7.70 (2H, d), 10.50 (3H, br) |
| 5490 | C$_{30}$H$_{30}$N$_4$O$_6$S | 575 (1), 440 (3), 288 (2), 122 (30), 72 (100) | CI | d$_6$-DMSO/200 MHz 2.19 (6H, s), 2.50 (2H, t), 3.13 (2H, t), 3.87 (3H, s), 5.34 (2H, s), 6.74 (1H, s), 6.76 (1H, s), 7.05–7.10 (3H, m), 7.34 (2H, d), 7.50 (2H, d), 7.74 (2H, d), 8.29 (2H, d), 10.20–10.35 (2H, br) |
| 5491 | C$_{23}$H$_{23}$N$_3$O$_4$S | | | d$_6$-DMSO 2.19 (6H, s), 2.50 (2H, t), 3.13 (2H, t), 6.08 (2H, s), 6.73 (2H, s), 6.98 (1H, d), 7.06 (1H, dd), 7.17 (1H, d), 7.35 (2H, d), 7.51 (2H, d), 10.28 (2H, brs) |
| 5497 | C$_{25}$H$_{26}$N$_4$O$_2$S | 447 (7) | CI | d$_6$-DMSO/400 MHz 2.46 (6H, s), 3.17–3.27 (4H, m), 3.85 (3H, s), 6.75 (1H, s), 7.06 (1H, s), 7.18 (1H, t), 7.27 (1H, t), 7.38 (2H, d), 7.48 (3H, m), 7.69 (1H, d), 8.13 (1H, s), 9.67 (1H, brs), 10.00 (1H, brs) |
| 5497.HCl | | | | d$_6$-DMSO/400 MHz 2.76 (6H, s), 3.17–3.26 (2H, m), 3.35–3.42 (2H, m), 3.83 (3H, s), 6.74 (1H, s), 7.07 (1H, s), 7.16 (1H, t), 7.26 (1H, t), 7.43 (2H, d), 7.45 (3H, m), 7.71 (1H, d), 8.13 (1H, s), 9.68 (1H, brs), 10.01 (1H, brs), 10.59 (1H, brs) |
| 5498 | C$_{28}$H$_{25}$N$_3$O$_2$S$_2$ | 500 (100) | CI | d$_6$-DMSO/400 MHz 2.17 (6H, s), 2.52 (2H, t), 3.05 (2H, t), 6.83 (1H, s), 7.20 (1H, d), 7.44 (1H, d), 7.46 (1H, s), 7.51–7.56 (4H, m), 7.96–8.02 (2H, m), 8.10–8.16 (2H, m), 8.63 (1H, s), 9.33 (1H, brs) |
| 5498.HCl | | | | d$_6$-DMSO/400 MHz 2.50 (2H, t), 2.79 (6H, s), 3.25 (2H, t), 6.85 (1H, s), 7.35 (1H, d), 7.48 (1H, s), 7.50–7.56 (5H, m), 7.95–8.00 (2H, m), 8.12–8.17 (2H, m), 8.63 (1H, s), 9.92 (1H, brs), 10.18 (1H, brs) |
| 5499 | C$_{25}$H$_{25}$N$_3$O$_3$S$_2$ | 480 (100) | DCI | d$_6$-DMSO/400 MHz 2.16 (6H, s), 2.49 (2H, t), 3.04 (2H, t), 3.95 (3H, s), 6.38 (1H, s), 7.06 (1H, s), 7.17 (1H, d), 7.33–7.40 (2H, m), 7.45–7.52 (2H, m), 7.71 (1H, d), 7.87 (1H, d), 7.96 (1H, d), 9.55 (1H, brs) |
| 5499.HCl | | | | d$_6$-DMSO/400 MHz 2.50 (2H, t), 2.77 (6H, s), 3.30 (2H, t), 3.95 (2H, s), 6.88 (1H, s), 7.07 (1H, s), 7.35 (1H, d), 7.40 (1H, t), 7.47–7.55 (3H, m), 7.73 (1H, d), 7.92 (1H, d), 8.01 (1H, d), 9.67 (1H, brs), 9.85 (1H, brs), 10.34 (1H, brs) |
| 5502 | C$_{19}$H$_{27}$N$_3$O$_2$S$_2$ | 394 (63) | CI | d$_6$-DMSO/400 MHz 0.92 (9H, s), 2.15 (6H, s), 2.22 (2H, d), 2.48 (2H, t), 3.01 (2H, t), 5.95 (1H, t), 6.80 (1H, s), 7.15 (1H, d), 7.37 (1H, d), 10.29 (1H, brs) |
| 5502.01 | C$_{19}$H$_{27}$N$_3$O$_2$S$_2$.HCl | | | d$_6$-DMSO/400 MHz 0.92 (9H, s), 2.22 (2H, d), 2.74 (6H, s), 3.22–3.29 (4H, m), 5.97 (1H, t), 6.84 (1H, s), 7.32 (1H, d), 7.44 (1H, d), 9.59 (1H, brs), 10.36 (1H, brs), 10.68 (1H, brs) |
| 5507 | C$_{25}$H$_{24}$N$_4$O$_3$S$_3$ | 525 (10) | DCI (NH$_3$) | d$_6$-DMSO 2.15 (6H, s), 2.48 (2H, t), 3.00 (2H, t), 6.75 (1H, s), 6.85 (1H, s), 7.15 (1H, d), 7.20–7.25 (1H, m), 7.40 (1H, d), 7.55 |

-continued

| No. | Mol. Formula | mass (intensity) | mode | solvent/field | ¹H nmr data δ (solvent/field) |
|---|---|---|---|---|---|
| 5527 | $C_{12}H_9NO_2S$ | 232 (100) | DCI (NH₃) | CDCl₃ | (2H, d), 7.78 (2H, d), 7.85 (1H, d), 8.02–8.05 (1H, m), 10.20 (1H, brs), 10.30 (1H, brs) 7.15–7.19 (1H, m), 7.60–7.68 (2H, m), 7.80 (2H, d), 7.82 (1H, s), 7.90 (2H, d), 10.00 (1H, s) |
| 5528 | $C_{18}H_{15}N_3O_4S$ | 370 (100) | DCI (NH₃) | d₆-DMSO | 2.50 (3H, s), 4.35 (2H, s), 6.95 (1H, s), 7.20–7.25 (1H, m), 7.60 (2H, d), 7.80 (2H, d), 7.85 (1H, d), 8.05 (1H, d), 10.28 (1H, brs), 10.30 (1H, brs) |
| 5508 | $C_{23}H_{29}N_3O_2S_2$ | 444 (29) | CI | d₆-DMSO/400 MHz | 0.84 (3H, s), 1.23 (3H, s+1H, m), 2.09 (1H, brs), 2.15 (6H, s) 2.28–2.34 (2H, m), 2.37–2.46 (2H, m), 3.01 (2H, t), 3.18–3.40 (2H, m), 6.00 (1H, br), 6.10 (1H, s), 6.82 (1H, s), 7.15 (1H, d), 7.39 (1H, d), 9.75 (1H, brs) |

| | | Mass spec data | | | Microanalysis | | |
|---|---|---|---|---|---|---|---|
| No. | Mol. Formula | mass (intesity) | mode | ¹H nmr data δ (solvent/field) | | Calc | Found |
| 5128 | $C_{22}N_{23}N_3O_2S$ | 393 (5), 322 (10), 149 (30), 117 (40) | EI | 2.18 (6H, s), 2.50 (2H, t), 3.11 (2H, t), 6.75 (1H, s), 6.78 (1H, s), 7.32–7.56 (9H, m), 10.23 (2H, brs). (d₆-DMSO/400 MHz) | C<br>H<br>N | 67.15<br>5.89<br>10.68 | 67.13 67.20<br>5.84 5.86<br>10.64 10.66 |
| 5253 | $C_{20}H_{21}N_3O_3S\cdot HCl$ | 384 (40) | DCI (NH₃) | 2.80 (6H, t), 3.29 (2H, t), 3.33 (2H, t), 6.64 (1H, s), 6.84 (1H, s), 6.91 (1H, d), 6.96 (1H. d), 7.35 (1H, m), 7.43 (2H, m), 7.55 (2H, d), 9.58 (1H, brs), 10.22 (1H, br), 10.28 (1H, brs). (d₆-DMSO/400 MHz) | C<br>H<br>N | 57.21<br>5.28<br>10.01 | 57.10 57.12<br>5.25 5.26<br>9.86 9.85 |
| 5286 | $C_{24}H_{23}N_3O_2S_2$ | 450 (100) | DCI (NH₃) | 2.15 (6H, s), 2.49 (2H, t), 3.02 (2H, t), 6.87 (1H, s), 6.94 (1H, s), 7.18 (1H, d), 7.43 (1H, d), 7.50–7.55 (2H, m), 7.63 (1H, d), 7.87–7.95 (3H, m), 8.10 (1H, s). (d₆-DMSO/400 MHz) | C<br>H<br>N | 64.12<br>5.16<br>9.35 | 63.95 64.21<br>5.03 5.06<br>9.18 9.20 |
| 5422 | $C_{22}H_{22}N_4O_4S\cdot HCl$ | 439 (50), 72 (100) | DCI (NH₃) | 2.90 (6H, s), 3.34–3.37 (2H, m), 3.45–3.55 (2H, m), 6.90 (1H, s), 6.96 (1H, s), 7.56 (2H, d), 7.66 (2H, d), 7.79 (1H, t), 8.02 (1H, d), 8.26 (1H, d), 8.44 (1H, s), 10.50–10.60 (2H, br), 10.92 (1H, brs). (d₆-DMSO/300 MHz) | C<br>H<br>N | 55.6<br>4.9<br>11.8 | 55.4<br>5.1<br>11.45 |
| 5423 | $C_{23}H_{22}F_3N_3O_2S\cdot HCl$ | 462 (100), 72 (95) | CI | 2.89 (6H, s), 3.32–3.37 (2H, m), 3.53–3.59 (2H, m), 6.88 (1H, s), 6.93 (1H, s), 7.56 (2H, d), 7.65 (2H, d), 7.74–7.76 (2H, m), 7.91 (1H, d), 7.96 (1H, s), 10.53 (1H, brs), 10.83 (1H, brs), 10.85–11.00 (1H, br). (d₆-DMSO/300 MHz) | C<br>H<br>N | 55.5<br>4.7<br>8.4 | 55.1<br>4.8<br>8.4 |
| 5424 | $C_{24}H_{28}N_4O_2S$ | 437 (100), 364 (30), 159 (25) | FAB (+) | 2.19 (6H, s), 2.50 (2H, t), 2.98 (6H, s), 3.13 (2H, t), 6.70–6.78 (4H, m), 7.34 (2H, d), 7.44–7.53 (4H, m), 10.07 (1H, s), 10.14 (1H, s). (d₆-DMSO/200 MHz) | C<br>H<br>N | 66.0<br>6.5<br>12.8 | 65.8<br>6.5<br>12.5 |
| 5424.HCl | $C_{24}H_{28}N_4O_2S\cdot HCl$ | 437 (100), 72 (90) | CI | 2.89 (6H, s), 3.07 (6H, s), 3.31–3.37 (2H, m), 3.51–3.56 (2H, m), 6.82–6.87 (4H, m), 7.54–7.56 (4H, m), 7.64 (2H, d), 10.19 (1H, s), 10.25 (1H, s), 10.70–10.85 (1H, br). (d₆-DMSO/300 MHz) | C<br>H<br>N | 60.9<br>6.2<br>11.8 | 60.9<br>6.4<br>12.0 |
| 5426 | $C_{23}H_{25}N_3O_2S_2$ | 440 (100), 367 (30) | FAB (+) | 2.28 (6H, s), 2.50 (3H, s), 2.50 (2H, t), 3.22 (2H, t), 6.84 (1H, s), 6.85 (1H, s), 7.40 (2H, d), 7.44 (2H, d), 7.60 (2H, d), 7.61 (2H, d), 10.41 (2H, brs). (d₆-DMSO/300 MHz) | C<br>H<br>N | 62.80<br>5.70<br>9.60 | 63.00<br>5.55<br>9.30 |
| 5426.HCl | $C_{23}H_{25}N_3O_2S\cdot HCl$ | 440 (20), 72 (100) | CI | 2.50 (3H, s), 2.86 (6H, s), 3.30 (2H, m), 3.50 (2H, m), 6.84 (1H, s), 6.85 (1H, s), 7.39 (2H, d), 7.54 (2H, d), 7.60 (2H, d), 7.64 (2H, d), 10.42 (1H, s), 10.45 (1H, s), 10.58 (1H, s). (d₆-DMSO/300 MHz) | C<br>H<br>N | 58.0<br>5.5<br>8.8 | 58.2<br>5.7<br>8.7 |
| 5427 | $C_{20}H_{20}ClN_3O_2S_2$ | 434 (100), 436 (35), 361 (20) | FAB (+) | 2.17 (6H, s), 2.50 (2H, t), 3.05 (2H, t), 6.76 (1H, s), 6.89 (1H, s), 7.19 (1H, d), 7.43–7.60 (5H, m), 10.20–10.60 (2H, br). (d₆-DMSO/200 MHz) | C<br>H<br>N | 55.35<br>4.6<br>9.7 | 55.4<br>4.5<br>9.4 |
| 5427.HCl | $C_{20}H_{20}ClN_3O_2S_2\cdot HCl$ | 436 (30), 434 (80), 72 (100) | CI | 2.84 (6H, s), 3.35 (4H, s), 6.86 (1H, s), 7.01 (1H, s), 7.44 (1H, d), 7.56–7.68 (5H, m), 10.0–10.4 (2H, br), 10.63 (1H, s). (d₆-DMSO/300 MHz) | C<br>H<br>N | 51.1<br>4.50<br>8.9 | 51.1 51.0<br>4.5 4.6<br>8.6 8.6 |
| 5428.HCl | $C_{20}H_{20}N_4O_4S_2\cdot HCl$ | 445 (100), 72 (90) | CI | 2.86 (6H, s), 3.37 (4H, s), 6.96 (1H, s), 7.04 (1H, s), 7.45 (1H, d), 7.62 (1H, d), 7.89 (2H, d), 8.34 (2H, d), 10.10–10.35 (1H, br), 10.35–10.80 (1H, br), 10.91 (1H, s). (d₆-DMSO/300 MHz) | C<br>H<br>N | 49.9<br>4.4<br>11.65 | 50.0<br>4.5<br>11.8 |
| 5429.HCl | $C_{21}H_{23}N_3O_2S_3\cdot HCl$ | 446 (30), 106 (40), 96 (30), 72 (100) | CI | 2.83 (6H, s), 3.34 (4H, s), 6.86 (1H. s), 6.99 (1H, s), 7.39 (2H, d), 7.43 (1H, d), 7.59 (3H, m), 10.10 (1H, s), 10.50 (2H, s). (d₆-DMSO/300 MHz) | C<br>H<br>N | 52.3<br>5.0<br>8.7 | 52.4<br>5.05<br>8.6 |
| 5430 | $C_{24}H_{29}N_3O_2S_2$ | 456 (100), 383 (20) | FAB (+) | 1.40 (9H, s), 2.26 (6H, s), 2.50 (2H, t), 3.13 (2H, t), 6.87 (1H, s), 6.97 (1H, s), 7.28 (1H, d), 7.50–7.61 (5H, m), 10.10–10.70 (1H, br). (d₆-DMSO/300 MHz) | C<br>H<br>N | 63.3<br>6.4<br>9.2 | 63.1<br>6.2<br>9.0 |
| 5430.HCl | $C_{24}H_{29}N_3O_2S_2\cdot HCl$ | 456 (5), 106 (60), 72 (100) | CI | 1.40 (9H, s), 2.80 (6H, s), 3.32 (4H, m), 6.87 (1H, s), 6.99 (1H, s), 7.42 (1H, d), 7.57 (5H, m), 10.15 (2H, s), 10.42 (1H, s). (d₆-DMSO/300 MHz) | C<br>H<br>N | 58.6<br>6.1<br>8.5 | 58.3<br>6.3<br>8.5 |
| 5431.HCl | $C_{21}H_{20}N_4O_2S_2\cdot HCl$ | 425 (50), 72 (100) | CI | 2.84 (6H, s), 3.37 (4H, s), 6.91 (1H, s), 7.03 (1H, s), 7.45 (1H, d), 7.61 (1H, d), 7.81 (2H, d), 7.97 (2H, d), 10.15–10.50 (1H, br), 10.50–11.00 (2H, br). (d₆-DMSO/300 MHz) | C<br>H<br>N | 54.7<br>4.6<br>12.15 | 54.6<br>4.7<br>12.3 |
| 5432 | $C_{20}H_{19}Cl_2N_3O_2S_2$ | 470 (75), 468 (100), 397 (10), 395 (20), 286 (10) | FAB (+) | 2.27 (6H, s), 2.50 (2H, t), 3.14 (2H, t), 6.83 (1H, s), 6.99 (1H, s), 7.29 (1H, d), 7.53 (1H, d), 7.58 (1H, m), 7.75 (1H, d), 7.89 (1H, d). (d₆-DMSO/300 MHz) | C<br>H<br>N | 51.3<br>4.1<br>9.0 | 51.3<br>4.15<br>9.1 |
| 5432.HCl | $C_{20}H_{19}Cl_2N_3O_2S_2\cdot HCl$ | 470 (40), 468 | CI | 2.86 (6H, s), 3.36 (4H, s), 6.84 (1H, s), 7.01 (1H, s), | C | 47.6 | 47.7 |

-continued

| | | | | | | |
|---|---|---|---|---|---|---|
| | | (45), 106 (45), 72 (100) | | 7.44 (1H, d), 7.58 (2H, m), 7.76 (1H, d), 7.89 (1H, d), 10.18 (1H, s), 10.35 (1H, s), 10.84 (1H, s). (d$_6$-DMSO/300 MHz) | H<br>N | 4.0 4.0<br>8.3 8.35 |
| 5433 | C$_{20}$H$_{20}$BrN$_3$O$_2$S$_2$ | 480 (100), 478 (95), 407 (20), 405 (15) | FAB (+) | 2.27 (6H, s), 2.50 (2H, t), 3.14 (2H, t), 6.84 (1H, s), 6.99 (1H, s), 7.29 (1H, d), 7.46 (1H, m), 7.53 (1H, d), 7.60–7.62 (2H, m), 7.84 (1H, s), 10.2–11.2 (1H, br). (d$_6$-DMSO/300 MHz) | C<br>H<br>N | 50.2 50.4<br>4.2 4.0<br>8.8 8.5 |
| 5434 | C$_{21}$H$_{20}$N$_4$O$_2$S$_2$ | 425 (100), 352 (20) | FAB (+) | 2.27 (6H, s), 2.50 (2H, t), 3.14 (2H, t), 6.88 (1H, s), 7.00 (1H, s), 7.29 (1H, d), 7.54 (1H, d), 7.69 (1H, t), 7.85–7.92 (2H, m), 8.11 (1H, s), 10.2–11.2 (1H, br). (d$_6$-DMSO/300 MHz) | C<br>H<br>N | 59.4 59.4<br>4.75 4.65<br>13.2 13.3 |
| 5437.HCl | | 428 (20), 72 (100) | CI | 2.89 (6H, s), 3.32–3.35 (2H, m), 3.44–3.53 (2H, m), 6.86 (1H, s), 6.87 (1H, s), 7.53–7.59 (4H, m), 7.63–7.68 (4H, m), 10.35–10.52 (2H, br), 10.58 (1H, s). (d$_6$-DMSO/300 MHz) | C<br>H<br>N | 56.9 56.8<br>5.0 5.0<br>9.05 9.2 |
| 5438.HCl | C$_{23}$H$_{25}$N$_3$O$_3$S.HCl | 424 (60), 96 (50), 72 (100) | CI | 2.77 (6H, s), 3.19–3.24 (2H, m), 3.39–3.44 (2H, m), 3.79 (3H, s), 6.76 (2H, s), 6.91 (1H, dd), 7.09 (2H, m), 7.33 (1H, t), 7.43 (2H, d), 7.55 (2H, d), 10.32 (1H, s), 10.34 (1H, s), 10.50–10.65 (1H, brs). (d$_6$-DMSO/300 MHz) | C<br>H<br>N | 60.1 60.4<br>5.7 6.0<br>9.1 9.1 |
| 5440 | C$_{26}$H$_{31}$N$_3$O$_2$S | 450 (100), 377 (40) | FAB (+) | 1.41 (9H, s), 2.29 (6H, s), 2.50 (2H, t), 3.22 (2H, t), 6.83 (1H, s), 6.86 (1H, s), 7.44 (2H, d), 7.52–7.60 (6H, m), 10.36 (2H, brs). (d$_6$-DMSO/300 MHz) | C<br>H<br>N | 69.5 69.5<br>6.95 7.05<br>9.35 9.15 |
| 5440.HCl | C$_{26}$H$_{31}$N$_3$O$_2$S.HCl | 450 (20), 106 (25), 72 (100) | CI | 1.40 (9H, s), 2.84 (6H, s), 3.28 (2H, m), 3.51 (2H, m), 6.85 (1H, s), 6.86 (1H, s), 7.59 (8H, m), 10.34 (1H, s), 10.42 (1H, s), 10.80 (1H, s). (d$_6$-DMSO/300 MHz) | C<br>H<br>N | 64.25 64.4<br>6.6 7.0<br>8.6 8.8 |
| 5460 | C$_{21}$H$_{23}$N$_3$O$_2$S$_2$ | 414 (100), 341 (25) | FAB (+) | 2.18 (6H, s), 2.35 (3H, s), 2.50 (2H, t), 3.04 (2H, t), 6.77 (1H, s), 6.89 (1H, s), 7.20 (1H, d), 7.25 (2H, d), 7.43–7.50 (3H, m), 10.10–10.40 (2H, br). (d$_6$-DMSO/200 MHz) | C<br>H<br>N | 61.0 61.2<br>5.6 5.5<br>10.2 9.9 |
| 5460.HCl | C$_{21}$H$_{23}$N$_3$O$_2$S$_2$.HCl | 414 (100), 72 (20) | CI | 2.44 (3H, s), 2.85 (6H, s), 3.36 (4H, s), 6.88 (1H, s), 7.00 (1H, s), 7.34 (2H, d), 7.45 (1H, d), 7.55–7.60 (3H, m), 9.95–10.15 (1H, br), 10.43 (1H, s), 10.60–10.80 (1H, br). (d$_6$-DMSO/300 MHz) | C<br>H<br>N | 56.1 56.4<br>5.4 5.1<br>9.3 9.1 |
| 5462.HCl | C$_{23}$H$_{22}$N$_4$O$_2$S.HCl | 419 (100), 72 (50) | CI | 2.79 (6H, s), 3.21–3.26 (2H, m), 3.39–3.44 (2H, m), 6.78 (2H, s), 7.44 (2H, d), 7.54 (2H, d), 7.86 (2H, d), 7.70 (2H, d), 10.46–10.55 (2H, brs), 10.66 (1H, s). (d$_6$-DMSO/300 MHz) | C<br>H<br>N | 60.7 60.7<br>5.1 5.1<br>12.3 12.1 |
| 5463.HCl | C$_{23}$H$_{25}$N$_3$O$_2$S.HCl | 408 (5), 72 (100) | CI | 2.33 (3H, s), 2.76 (6H, s), 3.18–3.23 (2H, m), 3.39–3.44 (2H, m), 6.75 (2H, s), 7.23 (2H, d), 7.42–7.47 (4H, m), 7.53 (2H, d), 10.24 (1H, s), 10.31 (1H, s), 10.55–10.70 (1H, s). (d$_6$-DMSO/300 MHz) | C<br>H<br>N | 62.2 62.35<br>5.9 6.0<br>9.5 9.35 |
| 5465.HCl | C$_{22}$H$_{21}$Cl$_2$N$_3$O$_2$S.HCl | 464 (50), 462 (60), 72 (100) | CI | 2.78 (6H, s), 3.19–3.29 (2H, m), 3.38–3.44 (2H, m), 6.72 (1H, s), 6.77 (1H, s), 7.43–7.55 (5H, m), 7.65 (1H, d), 7.78 (1H, d), 10.41 (2H, brs), 10.68 (1H, s). (d$_6$-DMSO/300 MHz) | C<br>H<br>N | 53.0 52.6<br>4.4 4.6<br>8.4 8.45 |
| 5470.HCl | C$_{19}$H$_{20}$N$_4$S$_2$O$_2$.HCl | | | 2.45 (6H, s), 2.75 (2H, m), 3.24 (2H, m), 6.79 (1H, s), 6.91 (1H, s), 7.32 (1H, d), 7.50 (1H, d), 7.80 (1H, t), 8.33 (1H, d), 8.65 (1H, d), 8.87 (1H, s), 10.12 (1H, brs), 10.54 (1H, brs), 10.88 (1H, brs). (d$_6$-DMSO/400 MHz) | | |
| 5477.HCl | | 458 (100), 385 (18), 199 (20) | FAB (+) | 2.86 (6H, s), 3.37 (4H, s), 3.98 (3H, s), 6.93 (1H, s), 7.03 (1H, s), 7.45 (1H, d), 7.61 (1H, d), 7.78 (2H, d), 8.07 (2H, d), 10.20 (1H, brs), 10.62 (1H, brs), 10.74 (1H, brs). (d$_6$-DMSO/300 MHz) | C<br>H<br>N | 53.49 53.80<br>4.90 5.09<br>8.51 8.88 |
| 5478 | | 452 (100), 379 (28) | FAB (+) | 2.89 (6H, s), 3.34 (2H, m), 3.54 (2H, m), 3.98 (3H, s), 6.89 (1H, s), 6.91 (1H, s), 7.56 (2H, d), 7.66 (2H, d), 7.78 (2H, d), 8.07 (2H, d), 10.56 (1H, s), 10.69 (1H, s), 10.78 (1H, brs). (d$_6$-DMSO/300 MHz) | C<br>H<br>N | 59.07 59.09<br>5.16 5.44<br>8.61 8.45 |
| 5479.HCl | C$_{23}$H$_{25}$N$_3$O$_3$S.HCl | 424 (100), 351 (31) | FAB (+) | 2.90 (6H, s), 3.32 (2H, m), 3.53 (2H, m), 3.90 (3H, s), 6.85 (1H, s), 6.86 (1H, s), 7.10 (2H, d), 7.55 (2H, d), 7.64 (4H, m), 10.36 (1H, s), 10.38 (1H, s), 10.66 (1H, brs). (d$_6$-DMSO/300 MHz) | C<br>H<br>N | 60.06 60.37<br>5.70 5.95<br>9.13 9.23 |
| 5480.HCl | C$_{22}$H$_{22}$BrN$_3$O$_2$S.HCl | 476 (25), 474 (25), 199 (100) | FAB (+) | 2.89 (6H, s), 3.32 (2H, m), 3.53 (2H, m), 6.83 (1H, s), 6.87 (1H, s), 7.63 (8H, m), 10.49 (1H, s), 10.58 (1H, s), 10.69 (1H, s). (d$_6$-DMSO/200 MHz) | C<br>H<br>N | 51.93 51.82<br>4.56 4.82<br>8.26 8.47 |
| 5481.HCl | C$_{29}$H$_{29}$N$_3$O$_3$S.HCl | 500 (100), 194 (54) | FAB (+) | 2.89 (6H, s), 3.22 (2H, m), 3.54 (2H, m), 5.27 (2H, s), 6.84 (1H, s), 6.85 (1H, s), 7.18 (2H, d), 7.54 (11H, m), 10.37 (2H, s), 10.86 (1H, brs). (d$_6$-DMSO/300 MHz) | C<br>H<br>N | 64.97 64.99<br>5.64 5.45<br>7.83 7.61 |
| 5482.HCl | | 506 (100) | FAB (+) | 2.86 (6H, s), 3.37 (4H, s), 5.27 (2H, s), 6.87 (1H, s), 6.99 (1H, s), 7.18 (2H, d), 7.54 (9H, m), 10.01 (1H, brs), 10.44 (1H, brs), 10.77 (1H, brs). (d$_6$-DMSO/300 MHz) | C<br>H<br>N | 59.82 59.89<br>5.21 4.41<br>7.75 7.63 |
| 5486.HCl | C$_{29}$H$_{29}$N$_3$O$_3$S.HCl | 500 (100), 427 (20), 154 (75), 136 (74) | FAB (+) | 2.90 (6H, s), 3.35 (2H, m), 3.55 (2H, m), 5.27 (2H, s), 6.85 (1H, s), 6.87 (1H, s), 7.10 (1H, dd), 7.23 (1H, d), 7.42 (1H, s), 7.51 (8H, m), 7.65 (2H, d), 10.46 (1H, s), 10.47 (1H, s), 10.86 (1H, s). (d$_6$-DMSO/300 MHz) | C<br>H<br>N | 64.97 64.90<br>5.64 5.61<br>7.83 7.85 |

| | | | | | |
|---|---|---|---|---|---|
| 5487 | | 506 (100), 433 (14) | FAB (+) | 2.86 (6H, s), 3.37 (4H, s), 5.26 (2H, s), 6.87 (1H, s), 7.01 (1H, s), 7.10 (1H, dd), 7.23 (1H, d), 7.31 (1H, s), 7.51 (8H, m), 10.11 (1H, brs), 10.53 (1H, brs), 10.60 (1H, brs). ($d_6$-DMSO/300 MHz) | C H N | 59.82 59.83<br>5.21 5.21<br>7.75 7.64 |
| 5491.HCl | $C_{23}H_{23}N_3O_4S \cdot HCl$ | 438 (100), 365 (28) | FAB (+) | 2.90 (6H, s), 3.32 (2H, m), 3.50 (2H, m), 6.18 (2H, s), 6.83 (1H, s), 6.85 (1H, s), 7.08 (1H, d), 7.17 (1H, d), 7.27 (1H, s), 7.54 (2H, d), 7.65 (2H, d), 10.39 (1H, brs), 10.39 (1H, s), 10.41 (1H, s). ($d_6$-DMSO/300 MHz) | C H N | 58.28 58.27<br>5.10 5.25<br>8.87 8.65 |
| 5494.HCl | $C_{30}H_{30}N_4O_6S \cdot HCl$ | 576 (100) | FAB (+) | 2.89 (6H, s), 3.34 (2H, m), 3.53 (2H, m), 3.95 (3H, s), 5.42 (2H, s), 6.84 (1H, s), 6.85 (1H, s), 7.19 (2H, m), 7.29 (1H, s), 7.54 (2H, d), 7.64 (2H, d), 7.82 (2H, d), 8.38 (2H, d), 10.40 (1H, s), 10.44 (1H, s), 10.74 (1H, s). ($d_6$-DMSO/300 MHz) | C H N | 58.96 58.58<br>5.11 5.09<br>9.17 9.11 |

We claim:

1. A diketopiperazine of formula (I):

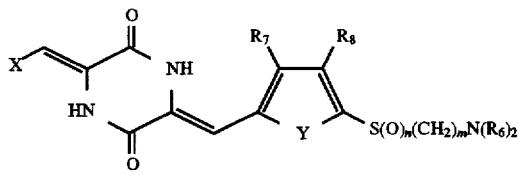

wherein each of $R_7$ and $R_8$ which may be the same or different, is hydrogen or a nitro group;

Y is

—O— or —S—, wherein each of $R_9$ and $R_{10}$, which may be the same or different, is hydrogen or a nitro group;

n is 0, 1 or 2;

m is an integer of 1 to 6;

each $R_6$, which may be the same or different, is a $C_1$–$C_6$ alkyl group; and X is selected from (i) a phenyl group of the following formula

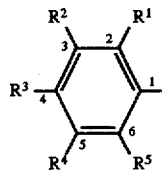

wherein each of $R^1$ to $R^5$, which may be the same or different, is independently selected from hydrogen, $C_1$–$C_6$ alkyl unsubstituted or substituted by one or more halogen atoms, $C_1$–$C_6$ alkoxy, $C_1$–$C_6$ alkythio, halogen, hydroxy, nitro, substituted phenyl, nitrobenzyl, benzyloxy, cyano, —$CH_2OH$, —$CH_2COOH$, —$CO_2R^{11}$, —$NHCOR^{14}$, —$NHSO_2R^{13}$, —$SO_2R^{13}$, —$CON(R^{11}R^{12})$, —$(CH_2)_xN(R^{11}R^{12})$, —$SOR^{13}$, —$SO_2N(R^{11}R^{12})$, —$N(R^{11}R^{12})$, —$O(CH_2)_xN(R^{11}R^{12})$, —$O(CH_2)_xCO_2R^{11}$, —$OCOR^{11}$, —$CH_2OCOR^{11}$, —$CH_2NHCOR^{11}$, —$CH_2NHCOOR^{13}$, —$CH_2SR^{11}$, —$CH_2SCOR^{11}$, —$CH_2S(O)_yR^{13}$, —$CH_2NHCO(CH_2)_xCO_2R^{11}$, —$N(R^{11})COR^{12}$, —$NHCOCF_3$, —$NHCO(CH_2)_xCO_2R^{11}$, —$NHCO(CH_2)_xOCOR^{11}$ and —$NHCO(CH_2)_xOR^{11}$ wherein x is 0 or is an integer of from 1 to 6, y is 1 or 2, each of $R^{11}$ and $R^{12}$, is independently, H or $C_1$–$C_6$ alkyl, $R^{13}$ is $C_1$–$C_6$ alkyl and $R^{14}$ is H, $C_1$–$C_6$ alkyl or a thiophene group; and/or any of $R_1$ and $R_2$, $R_2$ and $R_3$, $R_3$ and $R_4$ or $R_4$ and $R_5$, form together with the carbon atoms to which they are attached a furan group, a benzene ring or the cyclopentyl moiety of the group

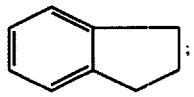

(ii) a heterocyclic ring selected from furan, thiophene, pyridine, quinoline and indole, the last of which is unsubstituted or N-substituted by $C_1$–$C_6$ alkyl;

(iii) a $C_1$–$C_6$ alkyl group, a 2,3-methylenedioxyphenyl group or a 3,4-methylenedioxyphenyl group; and (iv) a group —$(CH_2)_p$—Z wherein p is 0 or an integer of 1 to 4 and Z is a cyclohexyl group which optionally includes an unsaturated bond and/or a one or two carbon atom bridge, and is optionally substituted by one or more $C_1$–$C_6$ alkyl groups; or a pharmaceutically acceptable salt or ester thereof.

2. A compound according to claim 1 wherein X is a heterocyclic ring selected from 3-indole, 2-furan, 3-furan, 2-thiophene, 2-pyridine, 3-pyridine, 4-pyridine, 3-thiophene, 2-quinoline, 4-quinoline, 2-indole and 4-indole.

3. A compound according to claim 1 wherein the diketopiperazine has the following formula (A):

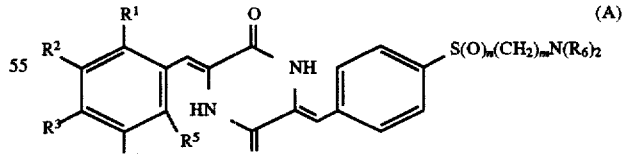

wherein $R_1$ to $R_6$ are as defined in claim 1, n is 0, 1 or 2 and m is 2 or 3.

4. A compound according to claim 1 wherein the diketopiperazine has the following formula (B)

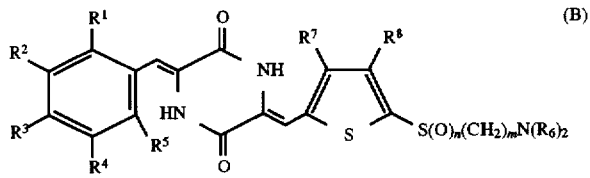

(B)

wherein $R_1$ to $R_8$ are as defined in claim 1, n is 0, 1 or 2 and m is 2 or 3.

5. A compound selected from:

(3Z,6Z)-3-(3-Chlorobenzylidene)-6-(4-(2-dimethylaminoethylthio)benzylidene)-2,5-piperazinedione (3Z,6Z)-3-(4-Dimethylaminobenzylidene)-6-(4-(2-dimethylaminoethylthio)benzylidene)-2,5-piperazinedione (3Z,6Z)-3-(3-Bromobenzylidene)-6-(4-(2-dimethylaminoethylthio)benzylidene)-2,5-piperazinedione (3Z,6Z)-3-(4-Chlorobenzylidene)-6-(4-(2-dimethylaminoethylthio)benzylidene)-2,5-piperazinedione (3Z,6Z)-3-(4-Cyanobenzylidene)-6-(4-(2-dimethylaminoethylthio)benzylidene)-2,5-piperazinedione (3Z,6Z)-3-(3,4-Dichlorobenzylidene)-6-(4-(2-dimethylaminoethylthio)benzylidene)-2,5-piperazinedione (3Z,6Z)-3-(3-Cyanobenzyidene)-6-(4-(2-dimethylaminoethylthio)benzylidene)-2,5-piperazinedione (3Z,6Z)-3-(4-Bromobenzylidene)-6-(4-(2-dimethylaminoethylthio)benzylidene)-2,5-piperazinedione (3Z,6Z)-3-(4-Benzyloxybenzylidene)-6-(4-(2-dimethylaminoethylthio)benzylidene)-2,5-piperazinedione (3Z,6Z)-3-(3-Benzyloxybenzylidene)-6-(4-(2-dimethylaminoethylthio)benzylidene)-2,5-piperazinedione (3Z,6Z)-3-(4-(2-Dimethylaminoethylthio)benzylidene)-6-(4-trifluoromethylbenzylidene)-2,5-piperazinedione (3Z,6Z)-3-(4-(2-Dimethylaminoethylthio)benzylidene)-6-(4-nitrobenzylidene)-2,5-piperazinedione (3Z,6Z)-3-(4-(2-Dimethylaminoethylthio)benzylidene)-6-(4-methylthiobenzyidene)-2,5-piperazinedione (3Z,6Z)-3-(4-(2-Dimethylaminoethylthio)benzylidene)-6-(4-tert-butylbenzylidene)-2,5-piperazinedione (3Z,6Z)-3-(4-(2-Dimethylaminoethylthio)benzylidene)-6-(4-methylbenzylidene)-2,5-piperazinedione (3Z,6Z)-3-(4-(2-Dimethylaminoethylthio)benzylidene)-6-(4-methoxycarbonylbenzylidene)-2,5-piperazinedione (3Z,6Z)-3-(4-(2-Dimethylaminoethylthio)benzylidene)-6-(4-methoxybenzylidene)-2,5-piperazinedione (3Z,6Z)-6-(4-(2-Dimethylaminoethylthio)benzylidene)-3-(3-furylmethylene)-2,5-piperazinedione (3Z,6Z)-6-(4-(2-Dimethylaminoethylthio)benzylidene)-3-(3-thienylmethylene)-2,5-piperazinedione (3Z,6Z)-6-(4-(2-Dimethylaminoethylthio)benzylidene)-3-(2-naphthylmethylene)-2,5-piperazinedione (3Z,6Z)-6-(4-(2-Dimethylaminoethylthio)benzylidene)-3-(3-nitrobenzylidene)-2,5-piperazinedione (3Z,6Z)-6-(4-(2-Dimethylaminoethylthio)benzylidene)-3-(3-trifluoromethylbenzylidene)-2,5-piperazinedione (3Z,6Z)-6-(4-(2-Dimethylaminoethylthio)benzylidene)-3-(3-methoxybenzylidene)-2,5-piperazinedione (3Z,6Z)-6-(4-(2-Dimethylaminoethylthio)benzylidene)-3-(3-methylbenzylidene)-2,5-piperazinedione (3Z,6Z)-6-(4-(2-Dimethylaminoethylthio)benzylidene)-3-(3-methoxy-4-(4-nitrobenzyloxy)benzylidene)-2,5-piperazinedione (3Z,6Z)-6-(4-(2-Dimethylaminoethylthio)benzylidene)-3-(3,4-methylenedioxybenzylidene)-2,5-piperazinedione (3Z,6Z)-6-(4-(2-Dimethylaminoethylthio)benzylidene)-3-(1-methyl-3-indolyl)methylene-2,5-piperazinedione (3Z,6Z)-6-Benzylidene-3-(4-(2-dimethylaminoethylthio)benzylidene)-2,5-piperazinedione (3Z,6Z)-6-Benzylidene-3-(4-(2-dimethylaminoethylsulphinyl)benzylidene)-2,5-piperazinedione (3Z,6Z)-6-Benzylidene-3-(4-(2-dimethylaminoethylthio)-3-nitrobenzylidene)-2,5-piperazinedione (3Z,6Z)-3-(5-(2-Dimethylaminoethylthio)-2-thienyl)methylene-6-(3-thienyl)methylene-2,5-piperazinedione (3Z,6Z)-3-(5-(2-Dimethylaminoethylthio)-2-thienyl)methylene-6-(3,4-methylenedioxybenzylidene)-2,5-piperazinedione (3Z,6Z)-3-(5-(2-Dimethylaminoethylthio)-2-thienyl)methylene-6-(2-naphthyl)methylene-2,5-piperazinedione (3Z,6Z)-3-(5-(2-Dimethylaminoethylthio)-2-thienyl)methylene-6-(4-trifluoromethylbenzylidene)-2,5-piperazinedione (3Z,6Z)-3-(5-(2-Dimethylaminoethylthio)-2-thienyl)methylene-6-(2-fluorenylmethylene)-2,5-piperazinedione (3Z,6Z)-6-(5-(2-Dimethylaminoethylthio)-2-thienyl)methylene-3-(4-quinolylmethylene)-2,5-piperazinedione (3Z,6Z)-6-(5-(2-Dimethylaminoethylthio)-2-thienyl)methylene-3-(2-quinolylmethylene)-2,5-piperazinedione (3Z,6Z)-3-(5-(2-Dimethylaminoethylthio)-2-thienyl)methylene-6-(3-methoxybenzylidene)-2,5-piperazinedione (3Z,6Z)-3-(5-(2-Dimethylaminoethylthio)-2-thienyl)methylene-6-(3-trifluoromethylbenzylidene)-2,5-piperazinedione (3Z,6Z)-3-(5-(2-Dimethylaminoethylthio)-2-thienyl)methylene-6-(3-nitrobenzylidene)-2,5-piperazinedione (3Z,6Z)-3-(5-(2-Dimethylaminoethylthio)-2-thienyl)methylene-6-(4-nitrobenzylidene)-2,5-piperazinedione (3Z,6Z)-3-(5-(2-Dimethylaminoethylthio)-2-thienyl)methylene-6-(4-methylthiobenzylidene)-2,5-piperazinedione (3Z,6Z)-3-(5-(2-Dimethylaminoethylthio)-2-thienyl)methylene-6-(4-tert-butylbenzylidene)-2,5-piperazinedione (3Z,6Z)-3-(5-(2-Dimethylaminoethylthio)-2-thienyl)methylene-6-(2-methylpropylidene)-2,5-piperazinedione (3Z,6Z)-3-(5-(2-Dimethylaminoethylthio)-2-thienyl)methylene-6-(2-(3,3-dimethylcyclohexyl)ethylidene)-2,5-piperazinedione (3Z,6Z)-3-(5-(2-Dimethylaminoethylthio)-2-thienyl)methylene-6-(4-methylbenzylidene)-2,5-piperazinedione (3Z,6Z)-3-(5-(2-Dimethylaminoethylthio)-2-thienyl)methylene-6-(4-methoxybenzylidene)-2,5-piperazinedione (3Z,6Z)-3-(5-(2-Dimethylaminoethylthio)-2-thienyl)methylene-6-(4-methoxycarbonylbenzylidene)-2,5-piperazinedione (3Z,6Z)-3-(5-(2-Dimethylaminoethylthio)-2-thienyl)methylene-6-(3-methoxy-4-(4-nitrobenzyloxy)benzylidene)-2,5-piperazinedione (3Z,6Z)-3-(5-(2-Dimethylaminoethylthio)-2-thienyl)methylene-6-(2-methoxy-1-naphthyl)methylene-2,5-piperazinedione (3Z,6Z)-3-(5-(2-Dimethylaminoethylthio)-2-thienyl)methylene-6-(3,3-dimethyl-1-butylidene)-2,5-piperazinedione (3Z,6Z)-3-(5-(2-Dimethylaminoethylthio)-2-thienyl)
methylene-6-(4-(2-thiophenecarboxamido)benzylidene)-
2,5-piperazinedione (3Z,6Z)-6-(5-(2-Dimethylaminoethylthio)-2-thienyl)
methylene-3-(3-pyridylmethylene)-2,5-piperazinedione (3Z,6Z)-6-(5-(2-Dimethylaminoethylthio)-2-thienyl)
methylene-3-(2-pyridylmethylene)-2,5-piperazinedione (3Z,6Z)-6-(5-(2-Dimethylaminoethylthio)-2-thienyl)
methylene-3-(4-pyridylmethylene)-2,5-piperazinedione (3Z,6Z)-6-(5-(2-Dimethylaminoethylthio)-2-thienyl)
methylene-3-(1-methyl-3-indolyl)methylene-2,5-
piperazinedione (3Z,6Z)-6-Benzylidene-3-(5-(2-diisopropylaminoethylthio)
-2-thienyl)methylene-2,5-piperazinedione (3Z,6Z)-6-Benzylidene-3-(5-(2-dimethylaminoethylthio)-4-
nitro-2-thienyl)methylene-2,5-piperazinedione (3Z,6Z)-3-(2,3-dihydro-5-benzofuranyl)methylene-6-(5-(2-
dimethylaminoethylthio)-2-thienyl)methylene-2,5-
piperazinedione (3Z,6Z)-6-Benzylidene-3-(5-(2-dimethylaminoethylthio)-2-
thienyl)methylene-2,5-piperazinedione (3Z,6Z)-6-(4-Acetamidobenzylidene)-3-(5-(2-
dimethylaminoethylthio)-2-thienyl)methylene-2,5-
piperazinedione (3Z,6Z)-6-(3-Chlorobenzylidene)-3-(5-(2-
dimethylaminoethylthio)-2-thienyl)methylene-2,5-
piperazinedione (3Z,6Z)-6-(2-Bromobenzylidene)-3-(5-(2-
dimethylaminoethylthio)-2-thienyl)methylene-2,5-
piperazinedione (3Z,6Z)-6-(4-Chlorobenzylidene)-3-(5-(2-
dimethylaminoethylthio)-2-thienyl)methylene-2,5-
piperazinedione (3Z,6Z)-6-(4-Cyanobenzylidene)-3-(5-(2-
dimethylaminoethylthio)-2-thienyl)methylene-2,5-
piperazinedione (3Z,6Z)-6-(3,4-Dichlorobenzylidene)-3-(5-(2-
dimethylaminoethylthio)-2-thienyl)methylene-2,5-
piperazinedione (3Z,6Z)-6-(3-Bromobenzylidene)-3-(5-(2-
dimethylaminoethylthio)-2-thienyl)methylene-2,5-
piperazinedione (3Z,6Z)-6-(3-Cyanobenzylidene)-3-(5-(2-
dimethylaminoethylthio)-2-thienyl)methylene-2,5-
piperazinedione (3Z,6Z)-6-Cyclohexylmethylene-3-(5-(2-
dimethylaminoethylthio)-2-thienyl)methylene-2,5-
piperazinedione (3Z,6Z)-6-(4-Benzyloxybenzylidene)-3-(5-(2-
dimethylaminoethylthio)-2-thienyl)methylene-2,5-
piperazinedione (3Z,6Z)-6-(3-Benzyloxybenzylidene)-3-(5-(2-
dimethylaminoethylthio)-2-thienyl)methylene-2,5-
piperazinedione (3Z,6Z)-6-(4-Bromobenzylidene)-3-(5-(2-
dimethylaminoethylthio)-2-thienyl)methylene-2,5-
piperazinedione (3Z,6Z)-6-(9-Anthrylmethylene)-3-(5-(2-
dimethylaminoethylthio)-2-thienyl)methylene-2,5-
piperazinedione (3Z,6Z)-6-Benzylidene-3-(5-(6-dimethylaminohexylthio)-
2-thienyl)methylene-2,5-piperazinedione (3Z,6Z)-6-Benzylidene-3-(5-(2-dimethylaminoethylthio)-2-
furyl)methylene-2,5-piperazinedione (3Z,6Z)-3-(5-(2-Dimethylaminoethylthio)-2-thienyl)
methylene-6-(6,6-dimethyl-bicyclo[3.1.1]hept-2-enyl)
methylene-2,5-piperazinedione.

6. A pharmaceutical composition comprising a pharmaceutically acceptable carrier or diluent and, as an active principal, a compound as defined in claim 1.

7. A process for the preparation of a compound of formula (I), as defined in claim 1, the process comprising either (i) condensing a compound of formula (II)

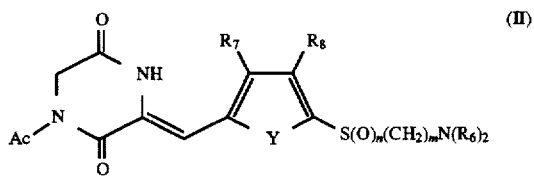

wherein Y, $R_6$, $R_7$, $R_8$, n and m are as defined above, with a compound of formula (III):

wherein X is as defined above and wherein any of the substituents on X is optionally protected, in the presence of a base in an organic solvent; or (ii) condensing a compound of formula (IV):

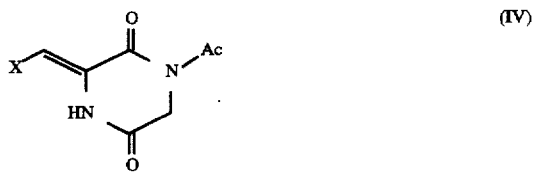

wherein X is as defined above and wherein any of the substituents on X is optionally protected, with a compound of formula (V):

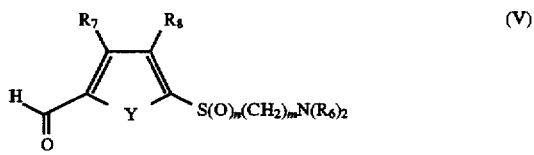

wherein Y, $R_6$, $R_7$, $R_8$, n and m are as defined above, in the presence of a base in an organic solvent; and, in either case (i) or (ii), if required, removing optionally present protecting groups and/or, if desired, converting one compound of formula (I) into another compound of formula (I), and/or, if desired, converting a compound of formula (I) into a pharmaceutically acceptable salt or ester thereof, and/or, if desired, converting a salt or ester into a free compound, and/or, if desired, separating a mixture of isomers of compounds of formula (I) into the single isomers.

8. A method of treating a patient in need of an inhibitor of PAI-1, which method comprises administering thereto a therapeutically effective amount of a compound which is a diketopiperazine of formula (I), as defined in claim 1, or a pharmaceutically acceptable salt thereof.

9. A method according to claim 8 which further comprises, when the patient is suffering from a thrombotic disorder, the simultanous separate or sequential administration of tPA.

* * * * *